(12) United States Patent
Vanlandingham et al.

(10) Patent No.: US 8,492,368 B2
(45) Date of Patent: Jul. 23, 2013

(54) NASAL DELIVERY MECHANISM FOR PROPHYLACTIC AND POST-ACUTE USE OF PROGESTERONE AND/OR ITS ENANTIOMER FOR USE IN TREATMENT OF MILD TRAUMATIC BRAIN INJURIES

(71) Applicants: Jacob W. Vanlandingham, Tallahassee, FL (US); John Suber, Tallahassee, FL (US); Michael Lewandowski, Odessa, FL (US)

(72) Inventors: Jacob W. Vanlandingham, Tallahassee, FL (US); John Suber, Tallahassee, FL (US); Michael Lewandowski, Odessa, FL (US)

(73) Assignee: Florida State University Research Foundation, Tallahassee, FL (US)

( * ) Notice: Subject to any disclaimer, the term of this patent is extended or adjusted under 35 U.S.C. 154(b) by 0 days.

(21) Appl. No.: 13/645,881

(22) Filed: Oct. 5, 2012

(65) Prior Publication Data
US 2013/0090316 A1    Apr. 11, 2013

Related U.S. Application Data

(60) Provisional application No. 61/544,502, filed on Oct. 7, 2011.

(51) Int. Cl.
*A61K 31/56* (2006.01)

(52) U.S. Cl.
USPC .......................................................... 514/177

(58) Field of Classification Search
USPC .......................................................... 514/177
See application file for complete search history.

(56) References Cited

U.S. PATENT DOCUMENTS

| | | | |
|---|---|---|---|
| 4,383,993 A | 5/1983 | Hussain et al. | |
| 4,596,795 A | 6/1986 | Pitha | |
| 5,089,482 A * | 2/1992 | Hermens et al. | 514/58 |
| 5,747,058 A * | 5/1998 | Tipton et al. | 424/423 |
| 6,923,988 B2 * | 8/2005 | Patel et al. | 424/489 |
| 2006/0147385 A1 | 7/2006 | Pike et al. | |

OTHER PUBLICATIONS

G. Rathnam et al., "Carbopol-based gels for nasal delivery of progesterone", AAPS PharmSciTech, vol. 9, No. 4, pp. 1078-1082, Dec. 2008.
G. Rathnam et al., "Preparation and evaluation of carbopol based nasal gels for systemic delivery of progesterone", International Journal Pharma. Research & Development—Online, vol. 2, Issue 1,pp. 1-11, Mar. 2010.
U.S. Appl. No. 13/645,854, filed Oct. 5, 2012.
U.S. Appl. No. 13/645,925, filed Oct. 5, 2012.
Pan, D. S., Liu, W. G., Yang, X. F., and Cao, F. (2007) Inhibitory effect of progesterone on inflammatory factors after experimental traumatic brain injury, Biomed Environ Sci 20, 432-438.
Jiang, C., Wang, J., Li, X., Liu, C., Chen, N., and Hao, Y. (2009) Progesterone exerts neuroprotective effects by inhibiting inflammatory response after stroke, Inflamm Res 58, 619-624.
Roof, R. L., Duvdevani, R., and Stein, D. G. (1992) Progesterone treatment attenuates brain edema following contusion injury in male and female rats, Restor Neurol Neurosci 4, 425-427.
Djebaili, M., Guo, Q., Pettus, E. H., Hoffman, S. W., and Stein, D. G. (2005) The neurosteroids progesterone and allopregnanolone reduce cell death, gliosis, and functional deficits after traumatic brain injury in rats, J Neurotrauma 22, 106-118.
Cutler, S. M., Cekic, M., Miller, D. M., Wali, B., VanLandingham, J. W., and Stein, D. G. (2007) Progesterone improves acute recovery after traumatic brain injury in the aged rat, J Neurotrauma 24, 1475-1486.
VanLandingham, J. W., Cekic, M., Cutler, S., Hoffman, S. W., and Stein, D. G. (2007) Neurosteroids reduce inflammation after TBI through CD55 induction, Neurosci Lett 425, 94-98.
Wright, D. W., Kellermann, A. L., Hertzberg, V. S., Clark, P. L., Frankel, M., Goldstein, F. C., Salomone, J. P., Dent, L. L., Harris, O. A., Ander, D. S., Lowery, D. W., Patel, M. M., Denson, D. D., Gordon, A. B., Wald, M. M., Gupta, S., Hoffman, S. W., and Stein, D. G. (2007) ProTECT: a randomized clinical trial of progesterone for acute traumatic brain injury, Ann Emerg Med 49, 391-402, 402 e391-392.
Xiao, G., Wei, J., Yan, W., Wang, W., and Lu, Z. (2008) Improved outcomes from the administration of progesterone for patients with acute severe traumatic brain injury: a randomized controlled trial, Crit Care 12, R61.
Stein, D. G. (2011) Is progesterone a worthy candidate as a novel therapy for traumatic brain injury?, Dialogues Clin Neurosci 13, 352-359.
Meaney, D. F., and Smith, D. H. (2011) Biomechanics of concussion, Clin Sports Med 30, 19-31, vii.
Chen, A. J., and D'Esposito, M. (2010) Traumatic brain injury: from bench to bedside [corrected] to society, Neuron 66, 11-14.
Tanielian, T. L., Jaycox, L., and Rand Corporation. (2008) Invisible wounds of war: psychological and cognitive injuries, their consequences, and services to assist recovery, RAND, Santa Monica, CA.
Kennedy, J. E., Jaffee, M. S., Leskin, G. A., Stokes, J. W., Leal, F. O., and Fitzpatrick, P. J. (2007) Posttraumatic stress disorder and post-traumatic stress disorder-like symptoms and mild traumatic brain injury, J Rehabil Res Dev 44, 895-920.
Oquendo, M. A., Friend, J. M., Halberstam, B., Brodsky, B. S., Burke, A. K., Grunebaum, M. F., Malone, K. M., and Mann, J. J. (2003) Association of comorbid posttraumatic stress disorder and major depression with greater risk for suicidal behavior, Am J Psychiatry 160, 580-582.
Gibson, C. L., Constantin, D., Prior, M. J., Bath, P. M., and Murphy, S. P. (2005) Progesterone suppresses the inflammatory response and nitric oxide synthase-2 expression following cerebral ischemia, Exp Neurol 193, 522-530.
Gibson, C. L., and Murphy, S. P. (2004) Progesterone enhances functional recovery after middle cerebral artery occlusion in male (Continued)

*Primary Examiner* — Raymond Henley, III
(74) *Attorney, Agent, or Firm* — Alchemy-Partners, PC; Ajay A. Jagtiani

(57) ABSTRACT

Compositions and methods for treating traumatic brain injury (TBI) and mild traumatic brain injury (mTBI) using progesterone and ent-progesterone are described.

17 Claims, 5 Drawing Sheets

OTHER PUBLICATIONS mice, J Cereb Blood Flow Metab 24, 805-813.

Shahrokhi, N., Khaksari, M., Soltani, Z., Mahmoodi, M., and Nakhaee, N. (2010) Effect of sex steroid hormones on brain edema, intracranial pressure, and neurologic outcomes after traumatic brain injury, Can J Physiol Pharmacol 88, 414-421.

O'Connor, C. A., Cernak, I., Johnson, F., and Vink, R. (2007) Effects of progesterone on neurologic and morphologic outcome following diffuse traumatic brain injury in rats, Exp Neurol 205, 145-153.

Kiraly, M., and Kiraly, S. J. (2007) Traumatic brain injury and delayed sequelae: a review—traumatic brain injury and mild traumatic brain injury (concussion) are precursors to later-onset brain disorders, including early-onset dementia, ScientificWorldJournal 7, 1768-1776.

Tran, H. T., LaFerla, F. M., Holtzman, D. M., and Brody, D. L. (2011) Controlled cortical impact traumatic brain injury in 3xTg-AD mice causes acute intra-axonal amyloid-beta accumulation and independently accelerates the development of tau abnormalities, J Neurosci 31, 9513-9525.

Shultz, S. R., Bao, F., Omana, V., Chiu, C., Brown, A., and Cain, D. P. (2012) Repeated mild lateral fluid percussion brain injury in the rat causes cumulative long-term behavioral impairments, neuroinflammation, and cortical loss in an animal model of repeated concussion, J Neurotrauma 29, 281-294.

Pettus, E. H., Wright, D. W., Stein, D. G., and Hoffman, S. W. (2005) Progesterone treatment inhibits the inflammatory agents that accompany traumatic brain injury, Brain Res 1049, 112-119.

Fleminger, S., Oliver, D. L., Lovestone, S., Rabe-Hesketh, S., and Giora, A. (2003) Head injury as a risk factor for Alzheimer's disease: the evidence 10 years on; a partial replication, J Neurol Neurosurg Psychiatry 74, 857-862.

Collins, M. W., Grindel, S. H., Lovell, M. R., Dede, D. E., Moser, D. J., Phalin, B. R., Nogle, S., Wasik, M., Cordry, D., Daugherty, K. M., Sears, S. F., Nicolette, G., Indelicato, P., and McKeag, D. B. (1999) Relationship between concussion and neuropsychological performance in college football players, JAMA 282, 964-970.

Iverson, G. L., Gaetz, M., Lovell, M. R., and Collins, M. W. (2004) Cumulative effects of concussion in amateur athletes, Brain Inj 18, 433-443.

Lewandowski, L., Rieger, B., Smyth, J., Perry, L., and Gathje, R. (2009) Measuring post-concussion symptoms in adolescents: feasibility of ecological momentary assessment, Arch Clin Neuropsychol 24, 791-796.

Binder, L. M. (1986) Persisting symptoms after mild head injury: a review of the postconcussive syndrome, J Clin Exp Neuropsychol 8, 323-346.

Wang, C., and Swerdloff, R. S. (2010) Hormonal approaches to male contraception, Curr Opin Urol 20, 520-524.

Mauvais-Jarvis, P., Kuttenn, F., and Baudot, N. (1974) Inhibition of testosterone conversion to dihydrotestosterone in men treated percutaneously by progesterone, J Clin Endocrinol Metab 38, 142-147.

VanLandingham, J. W., Cutler, S. M., Virmani, S., Hoffman, S. W., Covey, D. F., Krishnan, K., Hammes, S. R., Jamnongjit, M., and Stein, D.G. (2006) The enantiomer of progesterone acts as a molecular neuroprotectant after traumatic brain injury, Neuropharmacology 51, 1078-1085.

VanLandingham, J. W., Cekic, M., Hoffman, S. W., Cutler, S., Ory, D., Gale, S., Covey, D. F., and Stein, D. G. (2012) Progesterone activates the pregnane x receptor to reduce edema following traumatic brain injury.

Condon, J. C., Hardy, D. B., Kovaric, K., and Mendelson, C. R. (2006) Up-regulation of the progesterone receptor (PR)-C isoform in laboring myometrium by activation of nuclear factor-kappaB may contribute to the onset of labor through inhibition of PR function, Mol Endocrinol 20, 764-775.

Condon, J. C., Jeyasuria, P., Faust, J. M., Wilson, J. W., and Mendelson, C. R. (2003) A decline in the levels of progesterone receptor coactivators in the pregnant uterus at term may antagonize progesterone receptor function and contribute to theory: correlation with neuropsychological tests and delayed recovery, Neuroradiology 46. 550-558.

Guskiewicz, K. M., McCrea, M., Marshall, S. W., Cantu, R. C., Randolph, C., Barr, W., Onate, J. A., and Kelly, J. P. (2003) Cumulative effects associated with recurrent concussion in collegiate football players: the NCAA Concussion Study, JAMA 290, 2549-2555.

Schneiderman, A. I., Braver, E. R., and Kang, H. K. (2008) Understanding sequelae of injury mechanisms and mild traumatic brain injury incurred during the conflicts in Iraq and Afghanistan: persistent postconcussive symptoms and posttraumatic stress disorder, Am J Epidemiol 167, 1446-1452.

McKee, A.C., Gavett, B.E., Stern, R.A., Nowinski, C.J., Cantu, R.C., Kowall, N.W., Perl, D.P., Hedley-Whyte, E. T., Price, B., Sullivan, C., Morin, P., Lee, H.S., Kubilus, C.A., Daneshvar, D.H., Wulff, M., and Budson, A.E. (2010) "TDP-43 proteinopathy and motor neuron disease in chronic traumatic encephalopathy," J Neuropathol Exp Neurol 69, 918-929.

Abuznait, A. H., Cain, C., Ingram, D., Burk, D., and Kaddoumi, A. (2011) Up-regulation of P-glycoprotein reduces intracellular accumulation of beta amyloid: investigation of P-glycoprotein as a novel therapeutic target for Alzheimer's disease, J Pharm Pharmacol 63, 1111-1118.

van Assema, D. M., Lubberink, M., Bauer, M., van der Flier, W. M., Schuit, R. C., Windhorst, A. D., Comans, E. F., Hoetjes, N. J., Tolboom, N., Langer, O., Muller, M., Scheltens, P., Lammertsma, A. A., and van Berckel, B.N. (2011) Blood-brain barrier P-glycoprotein function in Alzheimers disease, Brain.

Vogelgesang, S., Cascorbi, I., Schroeder, E., Pahnke, J., Kroemer, H. K., Siegmund, W., Kunert-Keil, C., Walker, L. C., and Warzok, R. W. (2002) Deposition of Alzheimers beta-amyloid is inversely correlated with P-glycoprotein expression in the brains of elderly non-demented humans, Pharmacogenetics 12, 535-541.

Bartels, A. L., Willemsen, A. T., Kortekaas, R., de Jong, B. M., de Vries, R., de Klerk, O., van Oostrom, J. C., Portman, A., and Leenders, K. L. (2008) Decreased blood-brain barrier P-glycoprotein function in the progression of Parkinson's disease PSP and MSA J Neural Transm 115, 1001-1009.

Kooij, G., Backer, R., Koning, J. J., Reijerkerk, A., van Horssen, J., van der Pol, S. M., Drexhage, J., Schinkel, A., Dijkstra, C. D., den Haan, J. M., Geijtenbeek, T. B., and de Vries, H. E. (2009) P-glycoprotein acts as an immunomodulator during neuroinflammation, PLoS One 4, e8212.

Kushwaha, S., RK, K., and AK, R. (2011) Advances in nasal transmucosal drug delivery, Journal of Applied Pharmaceutical Science 1, 21-28.

Illum, L. (2000) Transport of drugs from the nasal cavity to the central nervous system, Eur J Pharm Sci 11, 1-18.

Hanson, L. R., Roeytenberg, A., Martinez, P. M., Coppes, V. G., Sweet, D. C., Rao, R. J., Marti, D. L., Hoekman, J. D., Matthews, R. B., Frey, W. H., 2nd, and Panter, S. S. (2009) Intranasal deferoxamine provides increased brain exposure and significant protection in rat ischemic stroke J Pharmacol Exp Ther 330, 679-686.

Kime, P. (2011) Nasal spray may prevent onset of seasickness, Navy Times.

McKinlay, A., Bishop, A., and McLellan, T. (2011) Public knowledge of 'concussion' and the different terminology used to communicate about mild traumatic brain injury (MTBI), Brain Inj 25, 761-766.

Fehm, H. L., Perras, B., Smolnik, R., Kern, W., and Born, J. (2000) Manipulating neuropeptidergic pathways in humans: a novel approach to neuropharmacology?, Eur J Pharmacol 405, 43-54.

Rockhill, C. M., Fann, J. R., Fan, M. Y., Hollingworth, W., and Katon, W. J. (2010) Healthcare costs associated with mild traumatic brain injury and psychological distress in children and adolescents, Brain Inj 24, 1051-1060.

Hua, F., Wang, J., Ishrat, T., Wei, W., Atif, F., Sayeed, I., and Stein, D. G. (2011) Genomic profile of Toll-like receptor pathways in traumatically brain-injured mice: effect of exogenous progesterone, J Neuroinflammation 8, 42.

Mantzoros, C. S., Georgiadis, E. I., and Trichopoulos, D. (1995) Contribution of dihydrotestosterone to male sexual behaviour, Bmj 310, 1289-1291.

Carson, C., 3rd, and Rittmaster, R. (2003) The role of dihydrotestosterone in benign prostatic hyperplasia, Urology 61, 2-7.

Cai, L. Q., Fratianni, C. M., Gautier, T., and Imperato-McGinley, J. (1994) Dihydrotestosterone regulation of semen in male pseudohermaphrodites with 5 alpha-reductase-2 deficiency, The Journal of clinical endocrinology and metabolism 79, 409-414.

Kelleher, C. C. (1990) Clinical aspects of the relationship between oral contraceptives and abnormalities of the hemostatic system: relation to the development of cardiovascular disease, American journal of obstetrics and gynecology 163, 392-395.

Vandenbroucke, J. P., Rosing, J., Bloemenkamp, K. W., Middeldorp, S., Helmerhorst, F. M., Bouma, B. N., and Rosendaal, F. R. (2001) Oral contraceptives and the risk of venous thrombosis, The New England journal of medicine 344, 1527-1.

Tas, E., Ozkan, Y., Savaser, A., and Baykara, T. (2004) In vitro and ex vivo permeation studies of chlorpheniramine maleate gels prepared by carbomer derivatives, Drug Dev Ind Pharm 30, 637-647.

Czeiter, E., Mondello, S., Kovacs, N., Sandor, J., Gabrielli, A., Schmid, K., Tortella, F., Wang, K. K., Hayes, R. L., Barzo, P., Ezer, E., Doczi, T., and Buki, A. (2012) Brain injury biomarkers may improve the predictive power of the IMPACT outcome calculator, J Neurotrauma 29, 1770-1778.

Cox, C. D., West, E. J., Liu, M. C., Wang, K. K., Hayes, R. L., and Lyeth, B. G. (2008) Dicyclomine, an M1 muscarinic antagonist, reduces biomarker levels, but not neuronal degeneration, in fluid percussion brain injury, J Neurotrauma 25, 1355-1365.

de Souza Silva, M. A., Topic, B., Huston, J. P., and Mattern, C. (2008) Intranasal dopamine application increases dopaminergic activity in the neostriatum and nucleus accumbens and enhances motor activity in the open field, Synapse 62, 176-184.

van den Berg, M. P., Verhoef, J. C., Romeijn, S. G., and Merkus, F. W. (2004) Uptake of estradiol or progesterone into the CSF following intranasal and intravenous delivery in rats, Eur J Pharm Biopharm 58, 131-135.

* cited by examiner

NASAL DELIVERY MECHANISM FOR PROPHYLACTIC AND POST-ACUTE USE OF PROGESTERONE AND/OR ITS ENANTIOMER FOR USE IN TREATMENT OF MILD TRAUMATIC BRAIN INJURIES

CROSS-REFERENCE TO RELATED APPLICATIONS

This application claims benefit of priority to U.S. Provisional Patent Application No. 61/544,502 to VanLandingham et al., entitled, "Prophylactic and Post-Acute Use of Progesterone and Its Enantiomer to Better Outcomes Associated with Concussion," filed Oct. 7, 2011, which is incorporated by reference in its entirety.

BACKGROUND

1. Field of the Invention

The present invention relates to prophylactic and post-acute treatments of concussions (mild TBI).

2. Related Art

There are many health issues related to traumatic brain injuries. For example, once an athlete sustains a concussion (one type of traumatic brain injury (TBI)) the athlete becomes four to six times more likely to suffer a second head injury. Also, half of deaths associated with falls in the elderly are caused by a head injury. In addition, a veteran commits suicide every 80 minutes and is 25 times more likely to develop Post-Concussion Syndrome (PCS) following TBI. Furthermore, cerebral plaques in head-injury patients are similar to cerebral plaques in Alzheimer's disease patients. One single TBI doubles the risk of Alzheimer's disease in males, and mild traumatic brain injury (mTBI) is the most common type of TBI that leads to long-term neurodegenerative disorders. The estimated annual cost of health care for traumatic brain injuries is $20 billion.

There are approximately 1.3 million cases of concussion reported each year in the United States. It is estimated that an additional 2 million cases of concussion are unreported. There are about 600,000 sports-related concussions per year. There have also been about 360,000 overseas military personnel who have suffered concussions, often due to the effects of detonation of improvised explosive devices (IEDs).

It is estimated that over 1.5 million people suffer traumatic brain injuries each year. Of these people who suffer traumatic brain injuries, it is estimated that over 50,000 die and that another 80,000 become impaired or disabled for life.

SUMMARY

According to a first broad aspect, the present invention provides a method comprising the following step: (a) administering a composition comprising progesterone to an individual within 15 minutes of the individual suffering a mild traumatic brain injury (mTBI).

According to a second broad aspect, the present invention provides a method comprising the following step: (a) administering a composition comprising ent-progesterone to an individual within 15 minutes of the individual suffering a mild traumatic brain injury (mTBI).

According to a third broad aspect, the present invention provides a method comprising the following step: (a) administering a composition to an individual by nasal administration, wherein the composition comprises ent-progesterone and one or more cyclodextrins, and wherein the molar ratio of ent-progesterone to the total amount of cyclodextrins in the composition is about 1:1.

According to a fourth broad aspect, the present invention provides a method comprising the following step: (a) administering a composition to an individual by nasal administration, wherein the composition comprises ent-progesterone and a bioadhesive polymer, and wherein molar ratio of ent-progesterone to the bioadhesive polymer in the composition is about 1:1.

According to a fifth broad aspect, the present invention provides a composition comprising ent-progesterone and one or more cyclodextrins, wherein molar ratio of ent-progesterone to the total amount of cyclodextrins in the composition is about 1:1.

According to a sixth broad aspect, the present invention provides a composition comprising ent-progesterone and a bioadhesive polymer, wherein molar ratio of ent-progesterone to the bioadhesive polymer in the composition is about 1:1.

According to a seventh broad aspect, the present invention provides a method comprising the following step: (a) administering a composition comprising ent-progesterone to an individual who has suffered a mild traumatic brain injury (mTBI), wherein step (a) is repeated at least daily for at least seven days.

BRIEF DESCRIPTION OF THE DRAWINGS

The accompanying drawings, which are incorporated herein and constitute part of this specification, illustrate exemplary embodiments of the invention, and, together with the general description given above and the detailed description given below, serve to explain the features of the invention.

DETAILED DESCRIPTION OF THE PREFERRED EMBODIMENTS

Definitions

Figure 1:
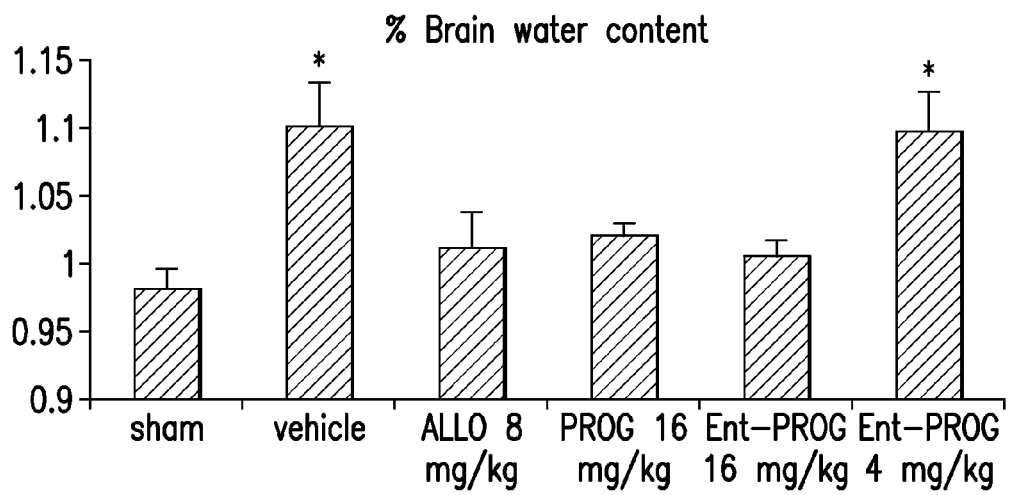
FIG. 1 shows a graph of percent brain water content for rats suffering from TBI that have been treated with allopregnanolone, progesterone and ent-progesterone.

Where the definition of terms departs from the commonly used meaning of the term, applicant intends to utilize the definitions provided below, unless specifically indicated. For the purposes of the present invention, a value or property is "based" on a particular value, property, the satisfaction of a condition, or other factor, if that value is derived by performing a mathematical calculation or logical decision using that value, property or other factor. For purposes of the present invention, the term "bioadhesive polymer" refers to a polymer that can increase bioavailability of ophthalmic, nasal, buccal, intestinal, rectal and vaginal formulations. One example of a bioadhesive polymer is carbopol.

For purposes of the present invention, the term "ent-progesterone component" and the term "ent-Prog component" refer to a component of a delivery system that contains ent-progesterone. The component may be a solution that contains ent-progesterone.

For purposes of the present invention, the term "individual" refers to a mammal. For example, the term "individual" may refer to a human individual.

For purposes of the present invention, the term "intranasal delivery" and term "intranasal administration" are equivalent terms and refer to the delivery or administration of a chemical composition through one or both nasal passages of an individual. Examples of intranasal delivery include actively spraying a chemical composition containing Prog or ent-Prog into a nasal passage, having an individual inhale a chemical mist containing Prog or ent-Prog.

For purposes of the present invention, the term "mild traumatic brain injury (mTBI)" refers to nondegenerative, non congenital insult to the brain from an external mechanical force that can lead to temporary or permanent cognitive, physical and psychosocial impairment with an associated diminished or altered state of consciousness.

For purposes of the present invention, the term "nasal spray" refers to a that functions by instilling a fine mist into the nostril by action of a hand-operated pump.

For purposes of the present invention, the term "progesterone component" and the term "Prog component" refer to a component of a delivery system that contains progesterone. The component may be a solution that contains progesterone.

For purposes of the present invention, the term "sham" and the term "sham control" refers to the members of a control group that are used to mimic a procedure or treatment without the actual use of the procedure or test substance.

For purposes of the present invention, the term "sprayable" refers to a solution that is turned into a fine mist by action of a hand operated pump.

For purposes of the present invention, the term "traumatic brain injury (TBI)" refers to an injury to the brain caused by an external mechanical force. A traumatic brain injury may be caused in various ways such as being exposed to a hit to the head while playing a sport such as football, hockey, baseball, etc.; being exposed to an explosion; being in a car accident; hitting one's head after a fall, etc.

For purposes of the present invention, the term "vehicle control" and "vehicle" refers to an animal that is subjected to a mild TBI and is treated with a drug formulation.

Description

In the description below, all ratios are by weight, unless specified otherwise.

Progesterone (Prog) has thus far been the most promising neuroprotective drug for the treatment of TBI: it reduces poor outcomes following injury by inhibiting inflammatory factors (TNF-α and IL-1β) and subsequently reducing brain edema (1, 2) Prog-treated rats have demonstrated significant improvements on a Neurological Severity Score (test for motor and cognitive functioning) following injury (3). Prog effectively attenuates edema in both rodent sexes following injury (4). Administering Prog or its derivative allopregnanolone (ALLO) also results in a decreased of the presence of the factors of cell death (caspase-3) and gliosis (GFAP) (5) following injury (6, 7). Formula 1 below shows the structure of progesterone.

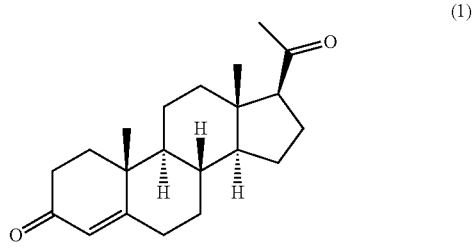

(1)

Phases I and II of the Prog for TBI clinical trial, ProTECT conducted at Emory University are complete. Results of this clinical trial using Prog to treat TBI have shown a 50% reduction in mortality in moderate to severe TBI patients receiving 72 hours of continuous intravenous Prog in the emergency room. This clinical trial has also measured 30 days post-injury outcomes using the Glasgow Outcome Scale-Extended and Disability Rating Scale scores. Moderate TBI patients who received Prog had better outcomes compared to those who did not receive the neurosteroid; there was little measurable difference in patients with severe brain injuries (8). However, a clinical study over the longer period of time of six months demonstrated that severe TBI patients had better neurological outcomes long-term when treated with Prog (9). The U.S. National Institutes of Health is now sponsoring nationwide Phase III clinical trials with Prog for 1200 moderate to severe TBI patients (10). Prog may extend its benefits by acutely treating military personnel with moderate to severe type TBIs from IED blasts.

Neurosteroids such as Prog have not been tested in an animal model that represents mTBI seen in military populations, even though mTBI accounts for more than 80% of all head injuries (11) and is now recognized as the most common neurological diagnosis (12). Approximately 360,000, which represent about 25%, of U.S. veterans of Iraq and; reports that mTBI is a serious yet often undiagnosed injury: this "silent epidemic" results in non-visible problems such as memory loss and depression; other symptoms include problems with concentration, lack of emotional control, headaches, fatigue, irritability, dizziness, blurred vision and seizures. It appears that repetitive mTBI may leave veterans at high risks for longer-term neuropsychological and neurodegenerative disorders (discussed below), decades after they exit the warzone; one such outcome is Post-Traumatic Stress Disorder (PTSD) associated with a high rate of suicide (13, 14).

With mTBI being the most common type of TBI affecting military personnel in one embodiment, the present invention provides a therapy using ent-Prog that may be administered repetitively and easily as a nasal spray in order to protect troops from potential harm and promote a safe and quicker return to duty post-injury.

The correlation between progesterone (Prog) intake following moderate to severe traumatic brain injury (TBI) and a reduction in cerebral inflammation and edema has been well documented (15-17). Prog also aids in improving short-term cognitive functions and motor coordination in a rodent model for TBI (5, 16, 18), and it has been shown to decrease the risk of subjects developing serious long-term diseases, such as Alzheimer's and Parkinson's (19, 20). While there has been extensive research on the benefits of administering Prog during moderate to severe TBI recovery, studies regarding the impact of Prog on the symptoms of mTBI—commonly known as concussion—have been extremely limited.

As with moderate to severe TBI, mild TBI has similar symptoms of inflammation, edema and decreased motor and cognitive functioning. Characteristic, yet not necessarily mutually exclusive, complications of mild TBI include: diffuse axonal injury; and repeated injury, a condition that causes cumulative neurological impairments known as chronic traumatic encephalopathy (CTE) (21). Past research supports acute administration of Prog for improving outcomes both in rodents and humans who have experienced moderate to severe TBI, however, Prog has never been used in the treatment of mild TBI.

In one embodiment of the present invention, Prog is administered acutely, within 15 minutes following a mild injury. A rodent model for concussion has been established (see Research Design and Methods section of Example 1 below) using memory impairment as the outcome measure (discussed below). In these studies Prog is used as a treatment to compare with vehicle (injured with no treatment) and sham (anesthesia and scalp incision only) groups of male Sprague Dawley Rats.

Laboratory and clinical research has demonstrated that progesterone (Prog) effectively reduces poor outcomes following traumatic brain injury by inhibiting inflammatory factors and subsequently reducing brain edema (1, 2)—however, studies in animals and humans with neuroprotective steroids have been limited to moderate and severe brain injury (4, 7, 22). Mild traumatic brain injuries account for more than 80% of all head injuries (10) and are now the most commonly diagnosed neurological condition (11). Even a single mild traumatic brain injury (mTBI) may cause long-term neurological dysfunction and has been determined to double the risk of developing Alzheimer's Disease (AD) in males (23). With multiple injuries, such as those endured by football players, boxers and wrestlers, neuropsychological performance decreases over time (24, 25); these individuals often suffer from Post-Concussion Syndrome (PCS) (26)—symptoms of which include problems with sleep, memory, attention, and cognition that often last years after injury (27). With about 25% or approximately 360,000 of the U.S. veterans of Iraq and Afghanistan having sustained mTBI (12), the likelihood of enduring multiple injuries from improvised explosive device (IED) blast waves is also high. Unfortunately, there has been little to no research with the use of neurosteroids in an animal model of mTBI or in humans, which continues to leave high-risk populations such as athletes and military personnel susceptible to suffering brain damage.

In one embodiment, the present invention provides a method for administering PROG acutely within 15 minutes following the individual suffering an mTBI.

Figure 7:
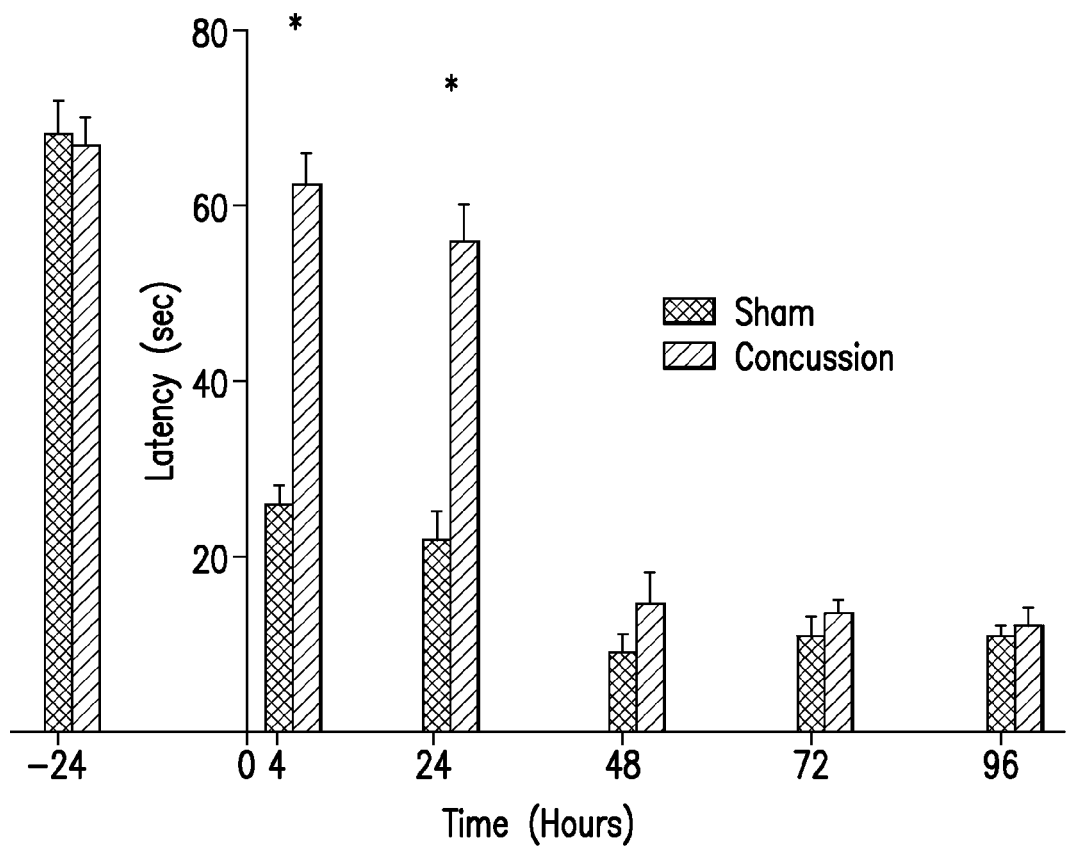
FIG. 7 shows a graph of latency to platform from Morris Water Maze Testing for rats that have and have not suffered a concussion.
Figure 8:
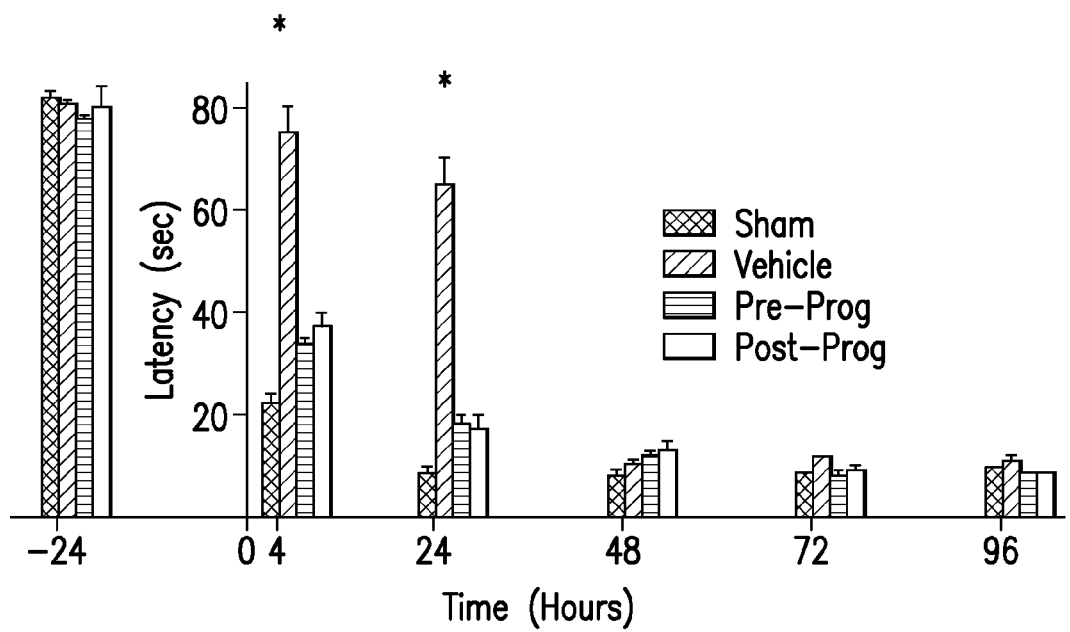
FIG. 8 shows a graph of latency to platform from Morris Water Maze Testing for rats that have suffered a concussion and been: (a) untreated, (b) treated with cyclodextrin, (c) prophylactically treated with progesterone and (d) post acutely-treated with progesterone and otherwise untreated.

Data demonstrates the validity of the above-described mTBI model and that Prog (prophylactic and post-acute administration) effectively treats and prevents the motor and cognitive sequelae of mTBI injury (See FIGS. 7 and 8). However, in order to reduce poor outcomes following repetitive mTBI and unreported singular mTBI, the drug must be administered on a repetitive basis to high-risk populations. Prog is not a sufficient prophylactic treatment for mTBI; in males it suppresses spermatogenesis, inhibits the conversion of testosterone to dihydrotestosterone, and reduces the size of reproductive organs (23, 28, 29). Previous research has shown that an alternative compound, known as the mirror-image or enantiomer of Prog (ent-Prog), bind to but does not activate the traditional progesterone receptor (PR), but operates via the pregnane x receptor (PXR), decreasing factors of inflammation and edema with equal efficacy to Prog, and increasing anti-oxidant activity better than does Prog (30, 31). While ent-Prog should not have the same sexual side effects as Prog, it does competitively inhibit the PR (30), so one potential consequence of using ent-Prog might be preventing pregnancy, or even inducing parturition (early onset of labor) in pregnant women (32, 33). Conflicting research has suggested that Prog and related compounds might also increase hypercoagulation, thus also increasing a thrombotic risk (34). Formula I below shows the structure of progesterone.

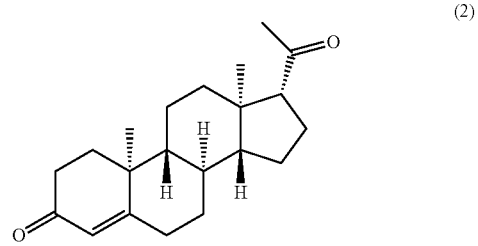

(2)

Figure 2:
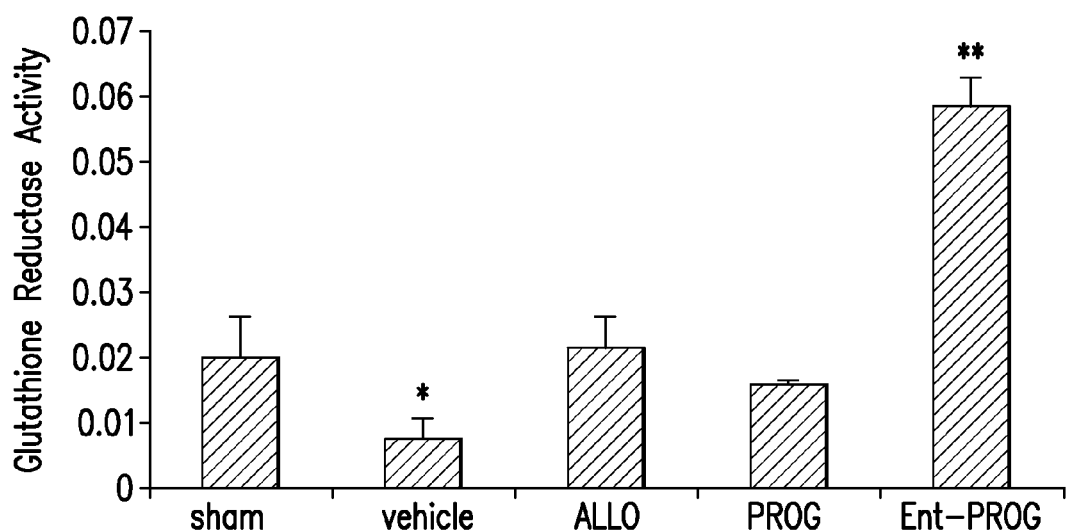
FIG. 2 shows a graph of glutathione reductase activity for rats suffering from TBI that have been treated with allopregnanolone, progesterone and ent-progesterone.

Pre-clinical data from a previous study (8) has shown that ent-Prog reduces moderate to severe brain injury-induced edema with equal efficacy to Prog (FIG. 1) and increases glutathione reductase (anti-oxidant) activity at a significantly higher rate than Prog (FIG. 2). FIG. 1 shows that ent-Prog (16 mg/kg) normalizes brain water content (measure of edema) as well as Prog and its metabolite, alloprenanolone (ALLO) at 72 hours post-injury. *denotes significance at p<0.05. FIG. 2 shows that ent-Prog significantly increases the anti-oxidant activity of glutathione reductase compared to all other groups post-injury at 72 hours post-injury. **denotes significance at p<0.01.

Figure 3:
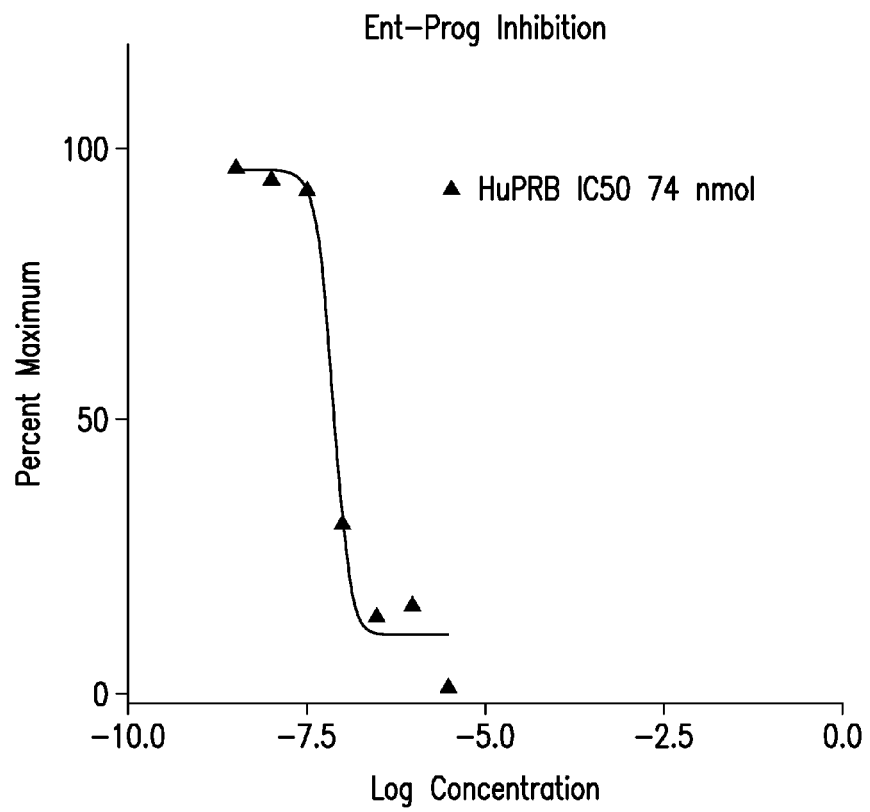
FIG. 3 shows a graph of the binding of ent-progesterone to the human progesterone receptor.

Although ent-Prog is correlated with factors associated with better outcomes following TBI, it does not activate the classical progesterone receptor (PR); in fact it even inhibits Prog binding to the PR (31): FIG. 3 depicts PR-binding assays. As the amount of ent-Prog increases, less Prog binds to the PR. Preliminary research currently being prepared for publication has identified a potential mechanism by which ent-Prog treats TBI: by activating a different receptor, for which Prog is also a ligand, called the pregnane X receptor (PXR). Both Prog and its enantiomer increased PXR-mediated transcription with equal efficacy (FIGS. 4 and 5); further, both neurosteroid treatments elevated the PXR activated P-glycoprotein (FIG. 6) (35). P-glycoprotein is a membrane channel that exports intracellular water and thus reduces cytotoxic edema associated with brain injury (36).

Figure 6:
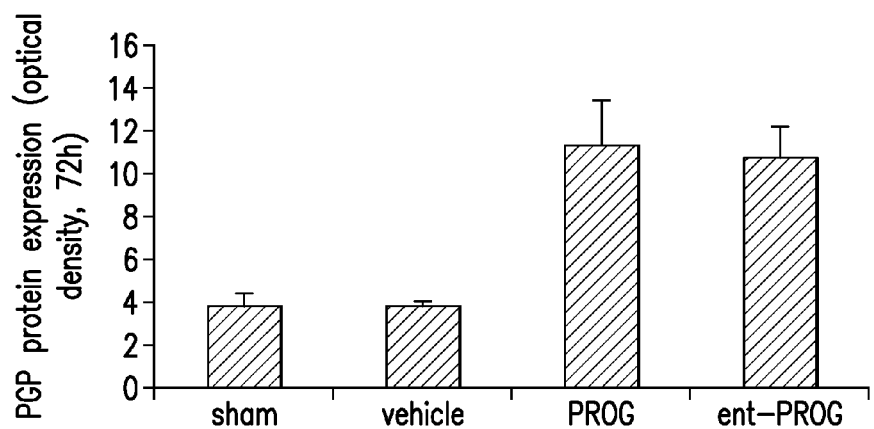
FIG. 6 shows a graph showing the effect of progesterone and ent-progesterone on increasing the protein abundance of P-glycoprotein in the penumbral region of an injured brain 72 hours after the brain has been injured.
Figure 4:
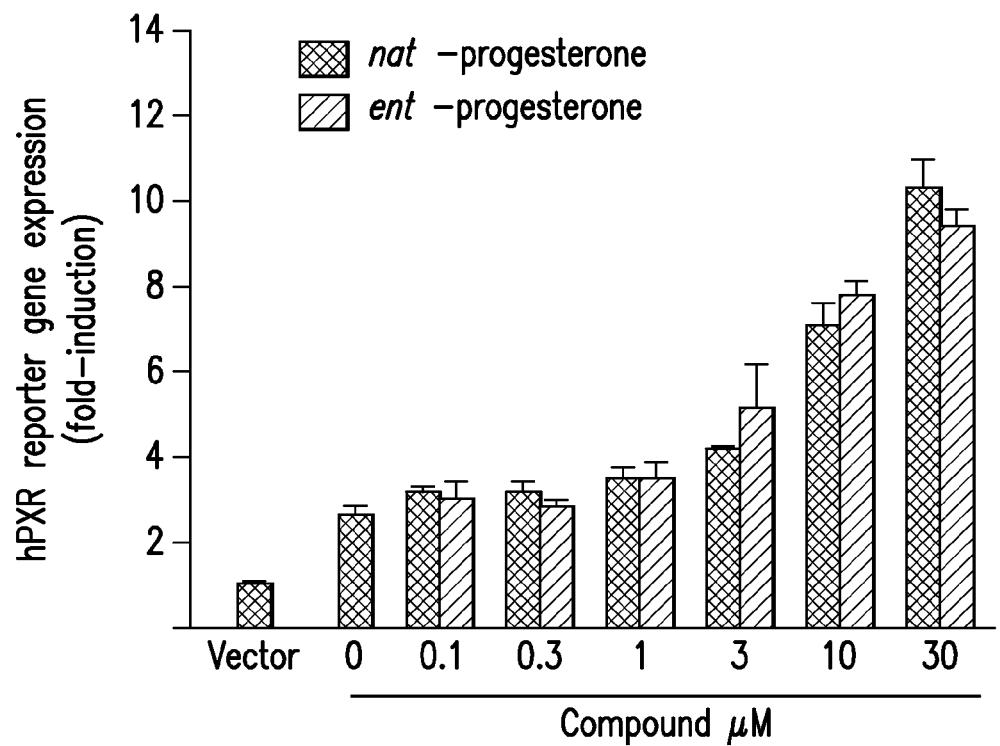
FIG. 4 shows a graph showing the effect of progesterone and ent-progesterone on human pregnane X receptor mediated transcription.
Figure 5:
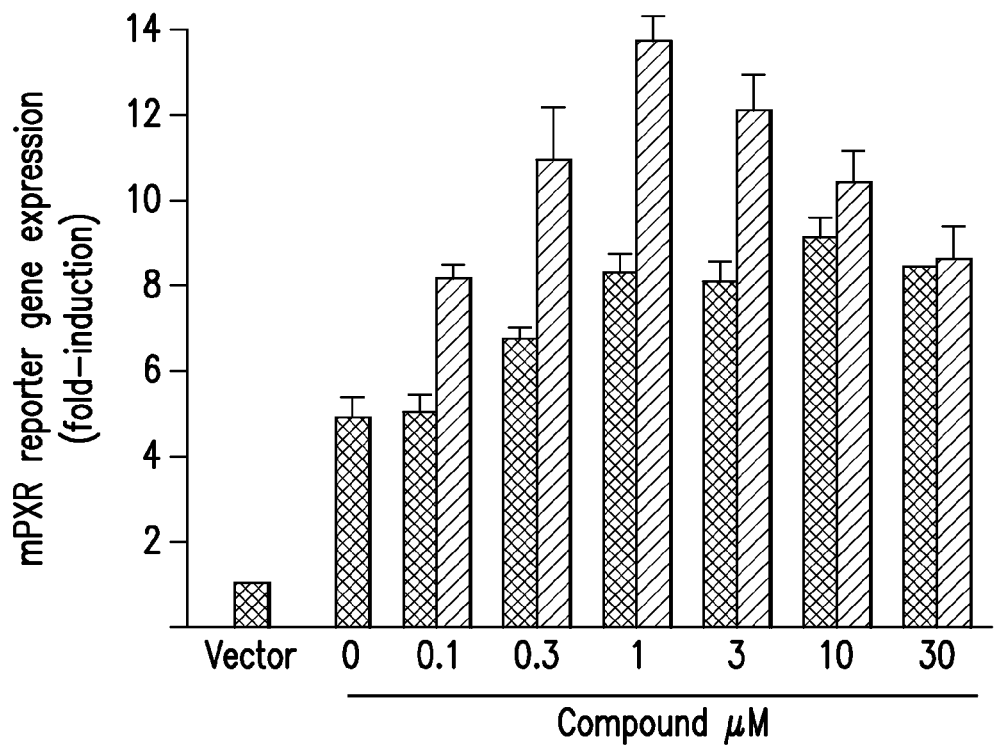
FIG. 5 shows a graph showing the effect of progesterone and ent-progesterone on mouse pregnane X receptor mediated transcription.

In FIG. 3 the data represents the percentage of Prog binding to the classical Human Prog receptor (PR) relative to maximum binding capacity under conditions of increasing ent-Prog administration. As shown in FIG. 3, ent-Prog significantly inhibits Prog binding to the PR FIGS. 4 and 5 show that increasing concentrations of Prog and ent-Prog increase both human and mouse PXR-mediated transcription with equal efficiency as measured by a luciferase gene reporter. As shown in FIG. 6, both Prog and ent-Prog increase the protein abundance of P-glycoprotein (PGP) in the penumbral region of the brain injury at 72 hours post-injury compared to no treatment (vehicle) and sham groups, respectively. *denotes significance at $p<0.05$.

PXR research with ent-Prog demonstrates that activation of the traditional PR is not necessary in order to effectively treat TBI. The widespread benefits and potential limitations of the differences in mechanisms between Prog and ent-Prog in the treatment of mTBI are discussed below.

There has been little to no research using therapeutics like Prog or other neurosteroids in an mTBI animal model. Using a controlled cortical impactor to induce injury in one mTBI model produces the data shown in FIG. 7. Rats that experience mTBI have greater latency to platform in comparison to sham using the Morris Water Maze swim test. These findings show that this mTBI model produces acute spatial learning and memory deficits.

FIG. 7 shows data collected from Morris Water Maze Testing. These data represent latency to platform in seconds. The points at −24 hours represent the training period; 0 hours is the time at which mTBI was induced; the first swim test after injury was performed at 4 hours. Start section (quadrant) varied day-to-day and trial-to-trial. *denotes significance at $p<0.05$.

The study proposed here is the first of its kind designed to treat mTBI in an animal model; there has been little research performed showing the effects of treatments in an mTBI animal model compared to the quantity of efficacy research performed in moderate to severe models. One early mTBI animal study correlated posttraumatic memory scores to neuronal loss; this was the first study to suggest an association between cognitive deficits following mTBI and neuropathological changes (37). A later study demonstrated persistent deficits in cognitive learning abilities and emergence of depressive-like behavior in injured mice similar to those reported in human Post-Concussion Syndrome (PCS) (38). Preliminary data, supported by the literature in this area, show that this mTBI model is valid.

Data indicates that this mTBI model can show the beneficial effects of neurosteroids, particularly Prog. When administered both prophylactically (15 minutes prior) and post-acutely (15 minutes post) Prog decreases latency to platform improving memory performance, in comparison to vehicle-injured rats (FIG. 8). Because of its similarities to Prog, ent-Prog should react similarly in this mTBI model.

FIG. 8 shows data collected from Morris Water Maze Testing. This data represents latency to platform in seconds. Significant beneficial differences between progesterone-treated (prophylactic (1 hour prior) and post-acute (1 hour post) and vehicle rats are apparent. *denotes significance at $p<0.05$.

TBI is characterized by primary mechanical injury followed by secondary neuronal cell death mediated by increased brain swelling (22, 39), inflammation (40) and oxidative stress (28). Both Prog and ent-Prog equivalently reduce factors of cell death, brain swelling and inflammation; however, ent-Prog has three times the antioxidant activity than does Prog—which provides potential mTBI victims with an added benefit. Since ent-Prog does not activate PR-mediated transcription but does activate the PXR, it presents a possible therapeutic alternative to Prog following brain injury (31). Benefits of the alternative compound include fewer sexual side effects than would be seen with Prog treatment in males, such as suppression of spermatogenesis; inhibition of the conversion of testosterone to dihydrotestosterone; and, reduction in the size of the testes, epididymis and leydig cells (29, 33, 41). ent-Prog competitively inhibits the PR (31), therefore a potential consequence of using ent-Prog as a TBI therapeutic involves inducing premature parturition in pregnant women (32, 34), or preventing pregnancy. There has also been conflicting data published on whether or not Prog or pregnane derivatives are associated with an increased thrombotic risk—thus studies may be designed to test for potential hyper-coagulative effects of the drugs tested (23).

Following the successful completion of this study, all the necessary testing in an animal model to ensure safety of use in clinical studies may be performed to confirm the safety of using ent-Prog as nasal inhalant to prophylactically prevent injury, as well as to post-acutely treat injury. Prog, due to the aforementioned side effects, potentially should not be used on a repetitive basis to prevent injury, which is undoubtedly a crucial factor when considering how to effectively treat repetitive mTBI. Even a single mTBI has been determined to double the risk of developing Alzheimer's disease (AD) in males (42)—and repetitive injuries increase these types of long-term risks and worsen the severity of symptoms of mTBI patients leading to even poorer outcomes upon reinjury. The reasons why ent-Prog may significantly improve long-term outcomes associated with mTBI are covered below.

When discussing long-term adverse outcomes following mTBI, the topic of repetitive injuries is highly relevant because the impact of each subsequent injury exponentially increases the severity of an individual's symptoms and the probability of developing serious neurological disorders. Kane and colleagues explain how repetitive injury leaves mTBI victims susceptible to developing PCS and advocates a need for therapeutic options. They discuss how longer deployment times, increases in the number of multiple redeployments, as well as improvements in body armor have led to many soldiers being exposed to numerous blast explosions and/or non-battlefield injuries, resulting in repetitive mTBIs (43). Unfortunately, repetitive mTBIs often go undiagnosed and do not show morphological abnormalities in the brain that can be detected by standard MRI brain scans (24, 44). Furthermore, recent findings show that amateur football players have multiple mTBIs that lead to a decline in neuropsychological performance compared to individuals with single or no concussions (25, 26, 45). Many individuals who suffer repetitive mTBIs experience PCS (46, 47). Unfortunately, the symptoms associated with PCS, which include disturbances with sleep, memory, attention, and cognition, persist sometimes for several years, and in other cases may be lifelong (27, 48-50). The symptoms of PCS are often resistant to current therapies (51).

Since PCS is so difficult to treat, it is important to establish a therapeutic protocol by which to follow in order to prevent the injury from occurring—or, treating it within a specified acute window of time post-injury. In a study of 12 Iraq war veterans with persistent PCS symptoms, veterans with mTBI exhibited decreased cerebral metabolic rates and also impairments in verbal fluency, cognitive processing speed, attention and working memory (52). In one embodiment, the present invention may prevent PCS from ever occurring using a safe and effective neurosteroid, ent-Prog. Prevention is also important to the health of a soldiers because concomitant mTBI and PTSD are associated with higher rates of other psychological health problems: depression (53), substance abuse (54), and suicidal behavior (55, 56). Individuals who have sustained TBI have an 8.1% chance of attempting suicide; whereas, there is a 1.9% chance in the general population (57). Among individuals receiving care through the Veterans Health Administration, compared to individuals without an injury history, mTBI patients were 1.98 times more likely to die by suicide; whereas, moderate to severe TBI patients were 1.34 times more likely to die by suicide. While moderate to severe injuries are more pathologically damaging at the time of injury, the psychological effects of mild injuries, especially when repetitive, may actually lead to more tragic outcomes (58).

A recent examination of the brains of National Football League players (59) and wrestlers (60) who have committed suicide as well as an Iraqi war veteran who committed suicide eight months after his honorable discharge from the USMC revealed no atrophy, contusions or hemorrhaging; the only condition noted was brain swelling. Upon further analysis, the work identified brain tissues that revealed Chronic Traumatic Encephalopathy (CTE)-changes such as tau-immunoreactive neurofibrillary tangles (NFTs) and neuritic threads (61). The tau-NFT pathology of mTBI suicide victims are very similar to that found in Alzheimer's disease (AD) patients. A neuroimaging study also discovered similarities between the pathology of AD and PTSD (62). The pathological similarities between PTSD and AD as well as AD and mTBI victims may explain why it is difficult to differentiate symptoms of PTSD and mTBI. With the same tauopathies that cause AD also contributing to mTBI with CTE, there has been a lot of research identifying mTBI with CTE having a higher propensity to cause AD (20, 63). The severity of AD has been associated with abnormal hyper-phosphorylated protein tau (hyper-$PO_4$ tau), containing aggregates of TDP-43 (64). Repetitive TBI with the development of CTE leads to abnormal TDP-43 expression in about 83% of cases (65). Even a single TBI nearly doubles the risk for AD in males only (42). The likeliest explanation for the gender difference in the risk of AD following head injury is the role of Prog; granted, with multiple head injuries characterized by CTE pathology, females do not have high enough levels of Prog to prevent adverse long-term outcomes. Nonetheless, ent-Prog may be as effective as or even more effective than Prog in preventing long-term neurodegenerative disorders; because, one proposed mechanism by which mTBI leads to AD is by a decrease in function of the PXR and subsequent decrease in PGP (66).

It has been shown that by activating PXR, both Prog and ent-Prog increased PGP by almost three times the levels as in the sham and vehicle rodents. Several diseases may benefit from an increase in the function of PGP, such as AD (65-67), Parkinson's disease (68) and Multiple Sclerosis (69). Prophylactic or acute treatment that increases activation of the PXR mechanism and subsequent cerebral PGP will benefit ent-Prog users by preventing mTBI poor outcomes from ever occurring and therefore eliminate the risk of future healthcare problems years and even decades later. With mTBI sometimes being difficult to diagnose—as well as patients neglecting to seek help for what appears to them to be a mild injury—in one embodiment of the present invention, veterans may use the drug as a preventative prophylactic one time per day when they are on overseas active duty. Of course, ent-Prog may still be used post-acutely following injuries when they occur but would be acting against the rapidly proliferating secondary cascade of the TBI. In order to facilitate ease of use, ent-Prog may be used as a nasal inhalant. There are also several potential benefits of using the neurosteroid as a nasal inhalant.

The nasal route of drug administration continues to receive increasing attention from pharmaceutical scientists and clinicians because this route circumvents hepatic first-pass elimination associated with oral delivery, is easily accessible and suitable for self-medication (70). Intranasal administration is also particularly suitable for drugs targeting the brain because certain drug solutions can bypass the blood-brain barrier (BBB) and reach the central nervous system (CNS) directly from the nasal cavity—uptake of these drugs depends on their molecular weight and lipophilicity (71, 72).

An example of a successfully developed nasal drug therapy for treatment of seasickness was previously funded by the Defense Medical Research and Development. Navy Times staff writer Patricia Kime describes in her article titled "Nasal spray may prevent onset of seasickness" a nasal spray that would deliver a preventative dose of motion sickness medication just before it may be needed. Kime further reports the nasal spray for seasickness could be effective with a lower concentration of the active ingredient scopolamine, which is more easily absorbed in the body intranasally—the lower concentration will mitigate drug side effects (73). Lower concentrations of ent-Prog may be needed, which will cause fewer to no noticeable side effects upon repetitive administration. Therefore, a prophylactic nasal spray of ent-Prog may be preferred to other drugs and drug delivery mechanisms.

Nasal delivery is one of the most attractive non-invasive routes for therapeutics targeting the central nervous system because of relatively high permeability of nasal epithelium membrane, avoidance of hepatic first pass elimination. Nasal delivery is easy to administer and allows for self-medication by an individual. Nasal mucociliary clearance is one of the most important limiting factors to nasal drug delivery. Nasal mucociliary clearance severely limits the time allowed for drug absorption to occur and may effectively prevent sustained drug administration. However, it has been documented that nasal administration of certain hormones has resulted in a more complete administration. In one embodiment, the present invention employs nasal delivery of Prog or ent-Prog for a more local delivery, thus avoiding any potential side effects of Prog or ent-Prog.

Cyclodextrins are cyclic oligosaccharides obtained from enzymatic degradation of starch. Cyclodextrins have been widely used to improve the delivery of drugs by nasal administration Improved nasal delivery has been attributed to changes in nasal mucosa permeability, alterations in drug solubility and in a change in the metabolism rate of the drugs at the site of delivery. Suitable cyclodextrins for use in compositions of the present invention include hydroxypropyl-$\beta$-CD (HP$\beta$-CD), hydoxypropyl-$\gamma$-CD (HP$\gamma$-CD), permethyl-$\beta$-CD (PM$\beta$-CD), and sulfobutylether-$\beta$-CD (SBE$\beta$-CD). In one embodiment of the present invention, a composition suitable for nasal administration, the ratio of cyclodextrin to Prog or ent-Prog may be about 1:1. In one embodiment of the present invention, a composition suitable for nasal administration, the ratio of cyclodextrin to Prog or ent-Prog may be about 2:1.

In one embodiment of the present invention, a composition containing Prog or ent-Prog that is suitable for nasal administration may include one or more bioadhesive polymers. Some polymers such as carbopol, can adhere onto the nasal mucosa for reasonably prolonged periods, preventing rapid nasal clearance. Bioadhesive polymers that may be used in the compositions of the present invention include 934, 940, 941, 942, 980 and 981. In one embodiment of the present invention, a composition suitable for nasal administration, the percentage of bioadhesive polymer in a suitable solution of Prog and ent-Prog may be 0.1%. In one embodiment of the present invention, a composition suitable for nasal administration, the percent of bioadhesive polymer in a suitable solution of Prog and ent-Prog may be 0.5%. In one embodiment of the present invention, a composition suitable for nasal administration, the percentage of bioadhesive polymer in a suitable solution of Prog and ent-Prog may be 1%.

In one embodiment of the present invention, a composition containing Prog or ent-Prog that is suitable for nasal administration may include one or more surfactants. Surfactants that may be used in the compositions of the present invention include different polyethylene glycols (PEGS). In one embodiment of the present invention, a composition suitable for nasal administration, the percent of surfactant in a suitable solution of Prog or ent-Prog may be 1%. In one embodiment of the present invention, a composition suitable for nasal administration, the percent of surfactant in a suitable solution of Prog or ent-Prog may be 2%. In one embodiment of the present invention, a composition suitable for nasal administration, the percent of surfactant in a suitable solution of Prog or ent-Prog may be 5%.

In one embodiment of the present invention, a composition containing Prog or ent-Prog that is suitable for nasal administration may include one or more buffering agents for controlling the pH of the composition. Buffering agents that may be used in the compositions of the present invention include citric acid and sodium citrate dihydrate. In one embodiment of the present invention, a composition suitable for nasal administration, the percent of buffering agent in a suitable solution of Prog or ent-Prog may be 0.001%. In one embodiment of the present invention, a composition suitable for nasal administration, the percent of buffering agent in a suitable solution of Prog or ent-Prog may be 0.005%.

The osmolarity of a composition of the present invention may be controlled by propylene glycol.

When a composition of the present invention is a gel, the composition may include a gelling agent such as hydroxylpropyl cellulose, carbopols, carboxymethylcellulose. And ethylcellulose A composition of the present invention may include a preservative such as ethylenediaminetetraacetic acid (EDTA) and benzalkonium chloride.

Suitable solvents for compositions of the present invention include water, vegetable oil and ethanol.

Past and preliminary data show that the novel neurosteroid, ent-Prog has the potential to be a viable prophylactic treatment for mTBI. The use of a nasal inhalant should reduce the concentration required to mitigate poor outcomes associated with mTBI and prevent unwanted side effects. Furthermore, nasal administration is a more practical means of delivery in a military setting.

In one embodiment, the present invention provides a method for improving the standard of care for military personnel with mild traumatic brain injury (mTBI) in the areas of prevention and treatment via a prophylactic and post-acute intranasal therapeutic. In one embodiment of the present invention, the active ingredients the therapeutic ent-Prog. Prog has been effective in the treatment of patients with moderate to severe brain injury. Ent-Prog may be a viable clinical alternative to Prog in treating mTBI with potentially fewer side effects. Since ent-Prog reduces adverse outcomes to injury as well as Prog does in an animal model of moderate to severe TBI, ent-Prog may be as effective as Prog in a mild injury model as well. There are a plethora of benefits to using ent-Prog in the treatment of mTBI—namely, the drug may be used prophylactically and regularly without having adverse side effects, compared to natural Prog. In one embodiment of the present invention, ent-Prog may be part of a formulation that is delivered intranasally to facilitate ease of access and use in the field and to minimize the dose required further limiting side effects. Using ent-Prog as a therapeutic may reduce poor outcomes following injury, especially neuropsychological and neurodegenerative disorders including Chronic Traumatic Encephalopathy (CTE) and Post-Traumatic Stress Disorder (PTSD) linked to repetitive brain injuries, an increasing concern for today's military personnel.

Despite the relatedness of Prog and ent-Prog, they are not identical compounds. For example, in contrast to Prog which may have various side effects when administered, ent-Prog may provide a safe treatment for the prevention of mTBI in high-risk populations with very few side effects.

Expected benefits of Prog treatment include: reduced cerebral inflammation, improved behavioral functioning, and reduced diffuse axonal injury.

Figure 9:
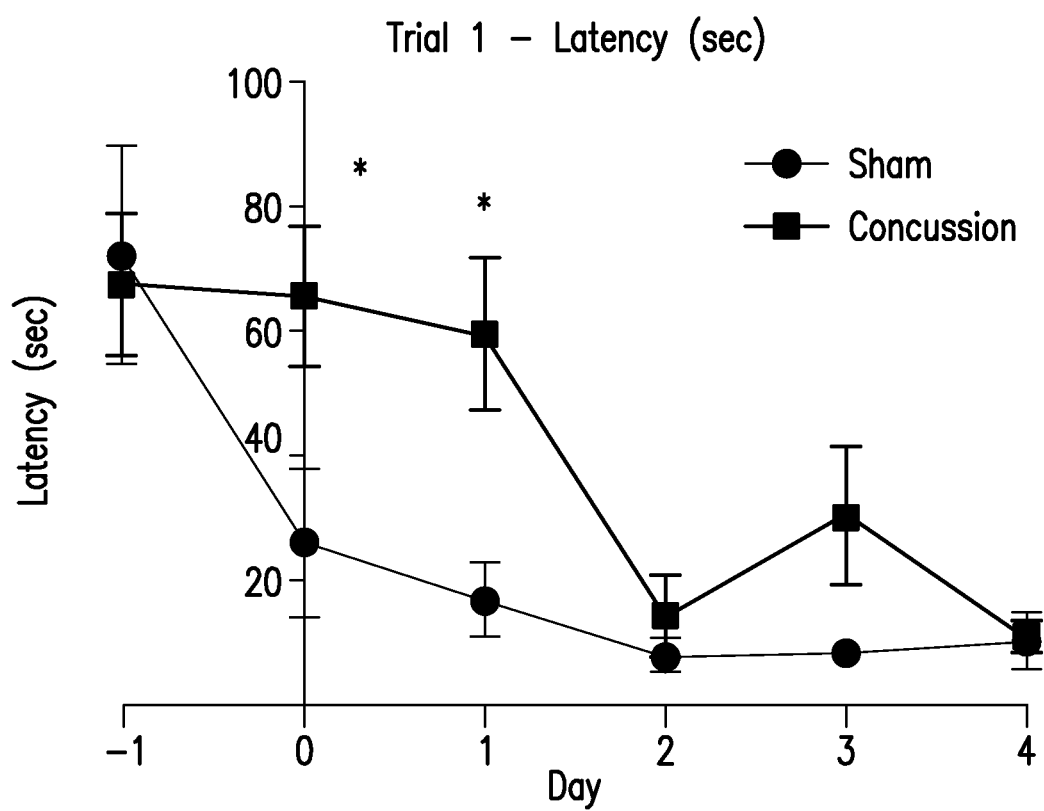
FIG. 9 is a graph showing the results for a Morris Water Maze Test for rats.

In one embodiment, the present invention provides a method to quickly treat concussed patients, especially athletes who endure sports-related and military-related injuries and risk experiencing repeated injury with compounded effects. According to some researchers, the majority of people do not recognize that a concussion is a brain injury, the consequences of which are also often misunderstood (74). The rapid administration of Prog following a mild head trauma may provide emergency medicine personnel a protocol to follow in the field; and, by increasing the percentage of mild TBIs treated, greater public awareness will follow. In FIG. 9 data points represent the latency to platform in seconds. Day 0 is the day of the hit. Day 0 through 4 are all post impacts. Start section (quadrant) varied day-to-day and trial-to-trial. In FIG. 9, "*" denotes significance at $p<0.05$.

In one embodiment, the present invention provides compositions that are nasal drops, eye drops and nasal sprays. For the nasal application, a solution or suspension may be used which is applied as spray, i.e., in the form of a fine dispersion in air or by means of a conventional pump.

In one embodiment, the present invention provides compositions comprising Prog or ent-Prog in the form of eye drops, nasal drops, or nasal spray. The nasal spray can, for example, be formed by the use of a conventional spray-squeeze bottle or a pump.

Suitable nontoxic pharmaceutically acceptable carriers for use in a drug delivery system for intranasal administration of Prog or ent-Prog may include carriers used for nasal pharmaceutical formulations for other steroids, such as estrogen. The choice of suitable carriers will depend on the exact nature of the particular nasal dosage form desired, e.g., whether Prog or ent-Prog is to be formulated into a nasal solution (for use as drops or as a spray).

Formulations of the present invention may contain a preservative and/or stabilizer. These include, for example: ethylene diamine tetraacetic acid (EDTA) and its alkali salts (for example dialkali salts such as disodium salt, calcium salt, calcium-sodium salt), lower alkyl p-hydroxybenzoates, chlorhexidine (for example in the form of the acetate or gluconate) and phenyl mercury borate. Other suitable preservatives are: pharmaceutically useful quaternary ammonium compounds, for example cetylpyridinium chloride, tetradecyltrimethyl ammonium bromide, generally known as "cetrimide", N-Benzyl-N,N-dimethyl-2-{2-[4-(2,4,4-trimethylpentan-2-yl)phenoxy]ethoxy}ethanaminium chloride, generally known as "benzethonium chloride" and myristyl picolinium chloride. Each of these compounds may be used in a concentration of 0.002 to 0.05%, for example 0.02% (weight/volume in liquid formulations, otherwise weight/weight). Preferred preservatives among the quaternary ammonium compounds are, however, alkylbenzyl dimethyl ammonium chloride and mixtures thereof, for example, the compounds generally known as "benzalkonium chloride".

According to one embodiment of the present invention there is provided a treatment strategy for athletes who have suffered a TBI that may not only reduce the time required for safe return to play but also provide protection from future mild TBIs.

Administering ent-Prog is a safe prophylactic treatment to administer before potential mTBIs occur. Intranasal (IN) administrations may have fewer side effects than intraperitoneal (IP) administrations due to a shift in pharmaceutical research to nasal sprays, drops and gels: the nasal route of drug administration continues to receive increasing attention from pharmaceutical scientists and clinicians because this route circumvents hepatic first pass elimination associated with oral delivery, is easily accessible and suitable for self-medication (70). Intranasal administration also particularly suits drugs targeting the brain because certain drug solutions can bypass the blood-brain barrier (BBB) and reach the central nervous system (CNS) directly from the nasal cavity—uptake of these drugs depends on their molecular weight and lipophilicity (71, 75). The intranasal delivery increases brain levels of the drug while decreasing systemic concentrations and thus should have less harmful side effects.

According to some researchers, the majority of people do not recognize that a concussion is a brain injury, the consequences of which are also often misunderstood (74). If ent-Prog is established as a safe treatment, the repetitive administration of this neurosteroid will prevent short-term and long-term poor outcomes and decrease costs to health care (76).

In one embodiment, the present invention provides a method of prophylactically administering ent-Prog to individuals who are involved in activities, such as contact sports or serving in the armed forces, where there is a possibility of the individuals suffering mTBI. In one embodiment, the present invention provides a method for acutely treating individuals who have suffered mTBI. For populations such athletes and military personnel, who have a high risk of suffering mTBI, ent-Prog may be made readily available for treatment when needed. Various delivery systems for ent-Prog including nasal delivery systems, intravenous (IV) delivery, etc. may be used to provide effective treatments strategies for individuals. For acute treatment strategies, nasal administration of ent-Prog may reduce the time for uptake and increase the concentration ent-Prog that reaches the brain. An advantage of ent-Prog over the use of Prog is that ent-Prog has fewer systemic side effects.

Having described the many embodiments of the present invention in detail, it will be apparent that modifications and variations are possible without departing from the scope of the invention defined in the appended claims. Furthermore, it should be appreciated that all examples in the present disclosure, while illustrating many embodiments of the invention, are provided as non-limiting examples and are, therefore, not to be taken as limiting the various aspects so illustrated.

EXAMPLES

Example 1

Specific Aims

Three specific aims are tested by Magnetic Resonance Imaging (MRI), behavioral testing and molecular analyses: (1) In order to evaluate a decrease in diffuse axonal injury, MR images are taken of the injured brain for Prog treated animals and compared to vehicle control groups at 24 hours and five days after injury. It is hypothesized that the lesion size in the right frontal cortex and diffuse axonal injury of processes connecting the right frontal cortex to the temporal cortex is reduced in treatment compared to the vehicle control group. (2) The animals also undergo behavioral tests for the first five days following injury including: water maze (learning, memory and anxiety-like behaviors and a balance beam (motor coordination). It is hypothesized that animals in the Prog treated group will achieve better post-injury functioning than the vehicle control group animals. (3) At 24 hours and following completion of the behavioral testing (five days), the animals are euthanized and their cerebral tissues analyzed for protein compositions. In a previous study, Prog down-regulated three specific genes that promote the inflammatory cascade following TBI: Bcl-2, IL-1β and Cxcl-10 (50, 77). Animal necropsies will thus include an evaluation of the proliferation of proteins coded for by the above genes, as well as the protein phospho-τ, which is traditionally up-regulated following TBI (20). It is expected that the damaged neuronal tissue of animals in the Prog treatment group to contain lower concentrations of these inflammatory signaling factors.

The results of the testing in this example may show that Prog treatment post-injury is effective at treating mild TBI if administered acutely.

Research Design and Methods

Animals and Progesterone Treatment: Sixty male Sprague Dawley rats are equally divided into three groups (n=20): (1) A treatment group that receives a mild TBI and Prog; (2) a vehicle group that undergoes mild TBI; and (3) a sham group that serves as a surgical control. Animals in the treatment group will receive intraperitoneal administration of Prog (16 mg/kg) 15 minutes postsurgery.

The vehicle treated group receive 2.5% cyclodextrin at the same 15 minute time point. Shams will not receive an injection. Thirty animals (n=10/group) undergo five days of behavioral testing and molecular analysis of inflammatory factors at five days post-injury. Eighteen animals (n=6/group) are used for 24 hour post-injury analysis of inflammatory factors. Twelve animals (n=4/group) are evaluated using MRI at both 24 hours and five days post-injury.

Mild Traumatic Brain Injury Model for Concussion: Prior to surgery, animals are anesthetized with an initial isoflurane (2-chloro-2-(difluoromethoxy)-1,1,1-trifluoro-ethane) induction for four minutes. The animal's scalp is shaved and cleaned with isopropanol and betadine. During the surgery, anesthesia is maintained with isoflurane. A medial incision is performed and the scalp is pulled back over the medial frontal plate. A 6 mm diameter, 1 mm thick rubber helmet is secured on the skull. The animal will then be secured bilaterally in the prone position on a metal platform at the sixth cervical vertebrae. The head of the animal is placed over a foam pad. An electrically controlled injury device with a 5 mm metal impactor is positioned over the rubber helmet. An impact speed of 6.2 m/s at a 11 degree angle from vertical is used to produce a closed head injury, similar to what occurs with human concussion where rotation of the head is required to induce diffuse axonal injury. Three closed head impacts is performed at the following times: zero, 30 minutes and 60 minutes. Animals is returned to a heated cage before being re-anesthetized for successive impacts. Animals in the sham group will receive a scalp incision with no impact and remain under anesthesia for the same duration as concussed rats.

Behavioral Testing

Morris Water Maze: A circular tank with a diameter of 133 cm is filled with opaque water to a depth of 64 cm. A platform (11 cm×11 cm) is submerged to a depth of 2 cm and placed approximately 28 cm from the wall of the pool in the center of the northeast quadrant. Each animal is pre-trained and then tested for five days. At the start of each trial, the rat is placed in the pool and allowed to swim until it reaches the platform. The performance of each rat is measured in terms of latency to platform, length of path to platform, and whether it swam mostly on the outside rim or near the center of the tank. The water maze test evaluates spatial learning, memory and anxiety.

Balance Beam: There are two balance platforms in this test: a curved platform and a linear platform; both have graded widths between 4 cm and 1 cm. The animals is tested for five consecutive days beginning on the first day post-surgery. The time it takes the rodents to transverse the beam and their number of slips is recorded. The balance beam evaluates motor control and balance.

Magnetic Resonance Imaging: A 21 Tesla magnet is used to examine the morphological effect of injury and treatment in the animal. Anesthesia induction is performed at 1.0 to 2.5% v/v using isoflurane gas in a closed induction chamber. Within four to five minutes the animal is removed from the induction chamber and placed inside the MRI scanner while maintaining a 1.0 to 1.5% v/v gas flow to the animal's nose. The typical MR imaging time is approximately one hour. Diffusion tensor imaging MR software is used to evaluate diffuse axonal injury by measure of axonal anisotropy (represents plasma membrane damage).

Diffusion weighted MR software is used to assess cerebral edema and lesion size. MR images is taken at 24 hours and five days following the injury. Effects of Prog treatment is ascertained when compared to vehicle control images.

Tissue Collection and Analysis: At 3 and 24 hours following injury, the animals is euthanized with $CO_2$ and decapitated for the collection of brain samples from the penumbra of the injury site. Analysis of inflammatory protein compositions is performed using Western Blotting and ELISA.

Statistical Analyses: The use of one-way ANOVA, t-tests, and Tukey-Kramer post hoc tests is used to determine significance set at $p<0.05$ when comparing all experimental groups.

The studies described above provide a foundation for the use of Prog acutely in humans who have sustained a mild TBI. Given that high risk populations have been identified (athletes and military personnel) Prog could be made readily available for treatment when needed. Additionally, nasal delivery method stand to further improve Prog as a treatment strategy for these high risk populations, given that this route reduces time for uptake and specifically increases brain concentrations with less systemic side effects.

Example 2

Summary

Prog and ent-Prog are administered both intranasally (IN) and intraperitoneally (IP) to both male and female Sprague Dawley Rats. These neurosteroids are used as a daily treatment for two, four and eight weeks. The outcomes of neurosteroid-treated rats with vehicle (vehicle-treated) and sham (untreated) rats will be compared. The sexual side effects in male and female rodents, as well as the coagulative effects in male rodents will also be investigated.

Specific Aim 1

Evaluating Male Sexual Function after Repeated Neurosteroid Treatments

In order to evaluate male sexual function following treatment, rodents are evaluated and compared to vehicle control groups at the end of 2 and 4 weeks. Male rodents are divided into 20 groups (n=3): daily Prog treated IP and IN at both 16 mg/kg and 32 mg/kg for 2 and 4 weeks; daily ent-Prog-treated IP and IN at 16 mg/kg and 32 mg/kg for 2 and 4 weeks; daily vehicle-treated for 2 and 4 weeks; and sham (untreated) for 2 and 4 weeks. Serum dihydrotestosterone (DHT) to testosterone ratios are measured, epididymal sperm concentrations, and relative reproductive organ weight of the testis, epididymis and prostate. It is crucial to determine that unlike Prog, ent-Prog does not lower DHT concentrations: DHT has been shown to be a major predictor of sexual activity in young men (78); it modulates prostatic function (79); and low DHT levels correlate with low semen volume and decreased motility (80). It is hypothesized that sexual functioning will be significantly better in ent-Prog-treated rodents than Prog-treated rodents and that the differences in side effects of these neurosteroids will be exacerbated with both an increase in concentration as well as length of treatment.

Specific Aim 2

Evaluating Blood Coagulation Post-Treatment

In order to evaluate coagulative effects of the neurosteroids, serum samples are taken at the end of each week, 2, 4 and 8. Rodents are divided into the same 20 groups (n=3) that are listed above in aim one. Blood are evaluated based on clotting time. The risk of Prog and Prog-related compounds causing coagulation has been explored mainly in studies involving over the counter birth control pills: some studies suggest that the risk of hypercoagulation can be attributed mainly to estrogen, while others suggest that Prog does increase the risk for those with a genetic predisposition for the disorder (81, 82). Assuming that Prog will have some hypercoagulative effects, it is hypothesized that the time to clot for ent-Prog groups will be greater than it will be for Prog groups. Furthermore, the differences in time to clot will increase with both neurosteroid concentration and length of treatment. It is also expected that IN groups to have fewer side effects than IP groups.

Collection/Analysis of DHT and Testosterone.

Plasma DHT and testosterone levels are measured by the ELISA method using DRG ELISA kits according to the standard protocol supplied by the kit manufacturer.

Collection and Measurement of Epididymal Sperm Concentration

The epididymal sperm concentration are determined according to the modified Turk method (83) cited in R. Bal and colleagues (84): The right epididymis is finely minced and allowed to incubate at room temperature for 4 hrs in isotonic saline. The solution is filtered and drawn into a capillary tube in which the dilution rate is measured. Then the solution is transferred to a hemocytometer counting chamber in which the sperm cells are counted with the help of a light microscope.

Collection and Weighing of Reproductive Organs

At end of treatment, males are euthanized. Testis, epididymis and ventral prostate are removed, cleared of adhering connective tissue and weighed. Relative weight of sexual organs is calculated by scaling to total body weight.

Serum for clotting times: Blood is collected following treatment cessation. Plasma is isolated and assayed for extrinsic and intrinsic clotting times. A microplate-based blood coagulation assay described by Pratt and Monroe (85) is performed by adding 30 µL plasma and 304 buffer (20 mM HEPES, 150 mM NaCl, 0.1% polyethylene glycol, pH 7.4) to wells of microplate which are then incubated at 25° C. for 2 min. Clotting is initiated by adding 30 µL1 of 5% thromboplastin in 25 mM $CaCl_2$ for the Prothrombin Time Test (extrinsic clotting cascade) and 30 µL activated partial thromboplastin reagent for the Activated Partial Thromboplastin Time Test (intrinsic clotting cascade). The increase in the turbidity of plasma is measured by the change in absorbance at 405 nm using kinetic microplate reader.

Male and Female Mating

At the onset of this study, female rodents are 63 days of age. For the first two weeks, vaginal smears are taken to verify rodent fertility. On the first day of week three, one untreated male rodent is paired with each female rodent. Every morning during the mating period, females are examined for the presence of sperm plugs or sperm in vaginal smears; if sperm is present, the females are tested for pregnancy. Females who are not pregnant are returned to the males. This procedure will continue for six more weeks (86). Females are monitored daily for signs of miscarriage. Litters born are examined for signs of viability.

Euthanization

At the end of treatment, rats are euthanized with $CO_2$.

Statistical Analyses

The use of one way ANOVA, t-tests, and Tukey-Kramer post hoc tests are used to determine significance set at $p<0.05$ when comparing all experimental groups within each design.

Example 3

Specific Aim 1

Determine the Intraperitoneal Dose and Time at which Prophylactic and Post-Acute Treatments with Progesterone and its Enantiomer Improve Responses to Mild Traumatic Brain Injury The efficacy of ent-Prog treatment for mTBI is determined and compared with natural Prog treatment. Based on past research with these two neurosteroids in a model of moderate to severe TBI it is hypothesized that an IP dose of 16 mg/kg at 1 hour after injury will provide optimal protection following mTBI. With regards to prophylactic treatment this same dosage will be most beneficial when given between 1 hour and 15 min prior to induction of mTBI based on previous research showing this timeframe to offer the optimal bioavailability of Prog. Furthermore, it is hypothesized that Prog and ent-Prog will equally improve responses to mTBI with greater efficacy seen with prophylactic administration. mTBI is induced in rats using a novel animal model applying closed head trauma to the right frontal plate of the skull with an electrically controlled impactor. Rats are injected intraperitoneally (IP, the standard method used in previous research) with three different concentrations of Prog or ent-Prog in order to determine the optimal dosage for prophylactic and post-acute administration. A window of time—for prophylactic treatment—is established in which the drugs are effective. Behavioral testing, imaging (edema), serum and brain drug concentrations, serum biomarker concentrations and pathological brain protein (markers for cell death, demyelination and inflammation) abundance are analyzed. The findings from this specific aim will establish criteria for efficacy as it relates to dose and time of drug administration before and after injury, respectively. Preliminary research has demonstrated that IP Prog improves behavioral outcomes when administered prior to and following mTBI. The work performed in this aim makes it possible to determine if ent-Prog is as protective as Prog for the treatment of mTBI given it stands to have limited to any side effects in comparison, especially when used on a repetitive basis in humans as a prophylactic. Drug synthesis, formulation and pharmacokinetic studies are also outlined in this specific aim.

Specific Aim 2

Determine the Intranasal Dose in which Prophylactic and Post-Acute Treatments with Progesterone and its Enantiomer Improve Responses to Mild Traumatic Brain Injury The efficacy of the intranasal (IN) administrations of Prog and ent-Prog is compared to that of IP analyzed in Specific Aim 1 of this example. Previous research has shown that N drug administration achieves better central nervous system delivery, crossing the blood brain barrier more efficiently than with IP administration. It is hypothesized that a significant reduction in IN dosage will have an equivalent positive response compared to the optimal IP dosage established in Specific Aim 1 of this example. Furthermore, it is hypothesized that a 4-fold reduction in dosage administered IN will show statistically higher efficacy than the optimal IP dosage established in Specific Aim 1 of this example. As in Specific Aim 1 it is hypothesized that Prog and ent-Prog will induce equivalent positive responses and prophylactic administration will be more advantageous than post-acute treatment. Rats are administered Prog and ent-Prog before and after the induction of mTBI as in Specific Aim 1. Prog and ent-Prog are administered within the prophylactic and post-acute windows of time for efficacy, outlined in Specific Aim 1. Both neurosteroids are administered IN at the most effective IP concentration identified in Specific Aim 1 of this example. Based on bioavailability studies outlined in Specific Aim 1 of this example, both drugs will also be administered at two lower concentrations than the most effective IP concentration. Testing methods identical to those described in Specific Aim 1 of this example are to establish efficacy following IN administration in this aim. The ultimate goal is to determine the optimal dose for IN drug administration that maximizes absorption from the cerebral circulation and minimizes delivery to the systemic circulation, while concomitantly reducing brain edema, cell death and demyelination. This aim is designed to determine if IN administration more effectively delivers Prog and ent-Prog to the brain than IP administration and which delivery method is more protective of the brain when given prior to versus following the insult. Furthermore as in Specific Aim 1 the experiments of Specific Aim 2 will aid in determining if ent-Prog and Prog are equally effective in the treatment of mTBI.

Specific Aim 3

Determine the Extent to which Prophylactic and Post-Acute Treatments with Progesterone and its Enantiomer Reduce Pathology Associated with Repetitive Mild Traumatic Brain Injury The efficacy of Prog and ent-Prog in an animal model of repeated mTBI is determined. It is hypothesized that the established optimal IN dose in Specific Aim 2 will equally maintain prophylactic and post-acute protection seen after a single injury when compared to a 4-injury repetitive mTBI model. Rats receive one impact weekly for four consecutive weeks. Prog and ent-Prog are delivered IN at the optimal time and dose determined in Specific Aim 2. Treatments are administered prophylactically and post-acutely as discussed in Specific Aims 1 and 2. Rats will receive varying numbers of treatments for the injury groups: for only the first injury, the first two injuries, the first three injuries, or all four injuries. Magnetic resonance imaging will evaluate the efficacy of treatment in terms of morphological effects (area of damage and edema), and behavioral testing will evaluate the efficacy of treatment in terms of motor and cognitive functioning following each injury. Temporal lobe brain slices are evaluated for tauopathy and Aβ-amyloid at 72 hours and 14 days following the final injury time point. This specific aim is designed to confirm if Prog and ent-Prog are valid treatment options and if so which one is more robust in a model of repetitive mTBI. Drug safety studies with respect to coagulation are also outlined in this specific aim.

Example 4

Mild Traumatic Brain Injury Model

Prior to surgery, animals are anesthetized with an initial isoflurane induction for 4 minutes—the minimum quantity of time necessary in order to mildly sedate the rodents during surgical preparation. The animal's scalp is shaved and cleaned with isopropanol and betadine. During the surgery, anesthesia is maintained with isoflurane. A medial incision is performed and the scalp is pulled back over the medial frontal cortex. A 6 mm diameter, 1 mm thick rubber helmet is placed on the skull and stabilized with bone wax. The animal is then secured in the prone position on the heated metal platform of the stereotaxic apparatus at the cervical $6^{th}$ and $7^{th}$ vertebrae. The head of the animal is placed over a foam pad. An electrically controlled injury device using a 5 mm metal impactor is positioned over the rubber helmet. An impact speed of 6.2 m/s at a 11° angle from vertical is used to produce a closed head injury, similar to what occurs with human concussion. The animal scalp is then sutured and analgesic applied. The animal is then returned to a heated cage in order to recover for 30 mins at which time food and water are provided. Animals in the sham group receive a scalp incision with no impact and remain under anesthesia for the same duration as concussed rats.

Specific Aim

Determine the Intraperitoneal Dose and Time at which Prophylactic and Post-Acute Treatments with Progesterone and its Enantiomer Improve Responses to Mild Traumatic Brain Injury It is hypothesized that intraperitoneal administration of the neurosteroids, Prog and ent-Prog are most beneficial when administered prophylactically in the treatment of a single mTBI. Past research using a model of moderate to severe TBI has shown that 16 mg/kg IP of both Prog and ent-Prog is the most beneficial concentration for reducing edema, inflammation, oxidative stress and cell death within the penumbral region at 72 hours following injury (1, 2). mTBI causes less mechanical damage and therefore a lower pathological response than moderate to severe brain injury. For these reasons administer 16 mg/kg are administered as the highest concentration and determine if lower IP concentrations (4 and 8 mg/kg) can achieve the same beneficial effects in a mild model of TBI. A dose response curve is developed based on drug-dose efficacy when analyzing cognitive behavior (spatial learning and memory and anxiety), motoric behavior (balance) and serum and brain biomarkers of injury.

Drug stability is tested over a six-month period when stored at both 4° C. and 25° C. After establishing the optimal drug formulation a pharmacokinetic profile is created for the bioavailability of each drug in the brain and serum for each route of administration.

Example 5

Drug Formulation and Stability

Design

Three formulations are developed; 2.25% β-cyclodextrin (β-CD) in $dH_2O$ plus drug (Prog or ent-Prog), Carbopol (1% in $H_2O$) plus drugs, 2.25% β-CD in $dH_2O$ plus Carbopol plus drugs. Prog-β-CD complex is commercially available (Sigma-Aldrich, St. Louis, Mo.), and carbopol is a known nasal absorption enhancer (87-89) thus potentially increasing bioavailability of Prog and ent-Prog. Carbopol will be added to water in which the required amount of drug-CD inclusion complex is dispersed by sonication. These polymeric dispersions are stirred in a magnetic stirrer for 60 min and the pH will be adjusted to 7.0 by adding triethanolamine. To determine the most soluble formulation small aliquots are taken and quantify changes in dynamic light scattering which represent precipitation/instability of the solution are quantified. Drug stability of defined formulations will also be monitored over a 1 year period. Briefly, stock solutions of each formulation are stored at 4 and 25° C. A small aliquot (1 mL) are tested every 14 days for changes in dynamic light scattering indicating precipitation/instability of the solution.

Example 5

Pharmacokinetic Studies of Bioavailability of Prog and Ent-Prog Using ELISA Subjects To determine the pharmacokinetic parameters of drug delivery for both Prog and ent-Prog to the brain 27 Sprague-Dawley rats at 280 g each are used (see Table 1). No brain injuries are performed on animals in this example.

TABLE 1

| | Optimal Formulation | | |
| --- | --- | --- | --- |
| Group | IP | IN | IV |
| Vehicle | 3 | 3 | 3 |
| Prog (16 mg/kg) | 3 | 3 | 3 |
| ent-Prog (16 mg/kg) | 3 | 3 | 3 |

Design

The bioavailability of Prog and ent-Prog is determined by measuring the serum Prog and ent-Prog abundance using a solid-phase enzyme immunoassay (ELISA). The optimal formulation determined in Example 5 above is administered using 16 mg/kg for IP and IN delivery. One group of rats will receive an intravenous (saphenous vein) injection of parenteral solution (16 mg/kg) to calculate the absolute bioavailability. Serial tail vein blood draws are performed at 30, 60, 120, 240, and 300 minutes after administration. Plasma is separated by centrifugation at 2,000 rpm and drug content determined by using an ELISA kit (Diagnostic Automation, Inc., Calabasas, Calif.) according to the manufacturer's protocol. Briefly, the assay is based on the principle of competitive binding between the drug in the test sample and drug-HRP conjugate. The pharmacokinetic parameters (area under the concentration-time curve from 0 to 300 min (AUC), peak concentration ($C_{max}$) and time to reach peak concentration ($t_{max}$) following vehicle, Prog and ent-Prog administration is calculated. The absolute bioavailability following IP or IN administration is determined by dividing the IP or IN AUC by the IV. AUC. Refer to Table 1 above for a breakdown of group design. (Total=27 animals).

Subject

To determine the optimal effective dose of Prog and ent-Prog when delivered IP in a model of mTBI 176 Sprague-Dawley rats at 280 grams are used.

Design

Groups (2 sets) will include sham, vehicle (determined by formulation studies outlined above), Prog and ent-Prog. Groups from set 1 will receive a single IP injection at 1 hours prior to mTBI and set 2 will receive a single IP injection at 1 hour post-mTBI. An IP injection at 1 hour post has been shown to be beneficial in moderate to severe TBI when using both Prog and ent-Prog. Preliminary data shows that Prog is beneficial when administered 1 hour prior to injury. However, an alternative strategy may be needed here with the addition of animals at a more immediate prophylactic time point to injury. Bioavailability studies assist in making changes to the time points of drug administration. Each set is composed of animals that receive one of three different IP concentrations of Prog or ent-Prog; 16 mg/kg, 8 mg/kg or 4 mg/kg.

Molecular Studies

Serum Analysis

Serum is collected at 3, 6, 24 and 48 hours post-injury using serial draws from the animal tail vein. Protein is processed and ELISA analysis are performed with the following antibodies: SBDP-150, and GFAP. Both of these serum biomarkers represent loss of integrity of the blood brain-barrier (BBB). SBDP-150 and GFAP also represent loss in neuronal and astrocyte structural integrity, respectively (90, 91). All serum samples are sent for preparation and analysis to Banyan Biomarkers, Inc. (Gainesville, Fla., see *Letters of Collaboration*). Serum analysis of drug concentration are performed on each animal from all groups at 1, 6, 24 and 48 hours following injury using a Prog and ent-Prog ELISA kit (Cayman Chemical, Ann Arbor, Mich.). No blood is taken prior to injury or before 1 hour post-injury as mTBI causes mild internal bleeding.

Brain Tissue Analysis

Brain tissue from the penumbral region of the impact and the hippocampus is collected by punch biopsy. Samples are processed for protein and Western analysis using antibodies for the cell death marker; caspase 3, demyelination marker; Myelin Basic Protein, and inflammatory markers; TNF-α and IL-1β. All markers of injury are analyzed at 6 and 48 hours post-injury. Briefly, all samples are collected, homogenized and incubated for 1 hour in TPer (Tissue protein extraction reagent) with 5% protease cocktail inhibitor. Protein concentration is determined spectrophotometrically using Nano-Drop at 280 nm. Equal protein concentration from each sample will separated using SDS PAGE and transferred onto a PVDF membrane. Appropriate primary and secondary antibodies are applied to each sample and a Molecular Imager used for detection and data analysis. Penumbral tissue analysis is justified to determine the secondary cascade of neuronal death and inflammation. Retrograde analysis of the hippocampus is required to determine the degree to which diffuse axonal injury has led to neuronal death and inflammation when the injury impact is to the frontal lobe (42, 92). Preliminary data shows that mTBI causes memory deficits.

This finding further justifies the analysis of the hippocampus in these studies.

Imaging Studies

Sodium Diffusion MRI is performed on animals from each treatment group at 6, 24 and 48 hours following injury to determine the level of brain edema. Diffusion Tensor MRI (See Facilities and Equipment) is performed on animals from each group to quantify diffuse axonal injury at the same time points. Table 2 below show a breakdown of the animals used in the Molecular Studies (Total=96 animals).

TABLE 2

Animal Use: Single mTBI, Molecular Studies

| Group | Prophylactic at 1 hr | Post-Injury at 1 hr |
|---|---|---|
| ent-Prog | n = 4 for each time point of sacrifice (2 times, 6 and 48 hr) and each dose (2). Total: 16 | n = 4 for each time point (2 times, 6 and 48 hr) and each dose (2) Total: 16 |
| Prog | n = 4 for each time point (2 times, 6 and 48 hr) and each dose (2). Total: 16 | n = 4 for each time point (2 times, 6 and 48 hr) and each dose (2). Total: 16 |
| Vehicle | n = 4 for each time point (2 times, 6 and 48 hr) Total: 8 | n = 4 for each time point (2 times, 6 and 48 hr) Total: 8 |
| Sham | n = 4 for each time point (2 times, 6 and 48 hr) Total: 8 | n = 4 for each time point (2 times, 6 and 48 hr) Total: 8 |

The same animals that survive for 48 hours (n=4/group) for brain tissue analysis are used for serum biomarker studies, serum drug concentration studies and MRI studies.

Cognitive and Motor Behavioral Studies

Improvements in functional outcomes associated with Prog and ent-Prog treatment are determined by analyzing spatial learning and memory (Morris Water Maze Testing), anxiety-like behaviors (Elevated Plus Maze) and balance (Beam and Rotorod,). See Facilities and Equipment page for outline of behavioral tests. Briefly, 2 pre-trial tests are performed each day starting 48 hours prior to the induction of mTBI. Following mTBI the testing using each method is initiated at 4 hours and performed every 24 hours for 5 days. Table 3 below provide a breakdown of the animals used in the Behavioral Studies (Total=80 animals).

TABLE 3

Animal Use: Single mTBI, Behavioral Studies

| Group | Prophylactic at 1 hr | Post-Injury at 1 hr |
|---|---|---|
| ent-Prog | n = 5 for each dose (3). Total: 15 | n = 5 for each dose (3) Total: 15 |
| Prog | n = 5 for each dose (3). Total: 15 | n = 5 for each dose (3). Total: 15 |
| Vehicle | n = 5 | n = 5 |
| Sham | n = 5 | n = 5 |

Example 8

Specific Aim

Determine the intranasal dose in which prophylactic and post-acute treatments with Progesterone and its Enantiomer improve responses to Mild Traumatic Brain Injury.

Hypothesis

Prophylactic intranasal administration of the neurosteroids, Prog and ent-Prog are more beneficial at lower concentrations than the optimal intraperitoneal dose when treating a single mTBI.

Rationale

The use of a nasal inhalant for the treatment of TBI is novel. Prog has been used as a nasal inhalant to investigate activity of dopaminergic neurons in rats (92) and there has been an ongoing interest in the nasal delivery of Prog for use in hormone replacement therapy and contraceptives (93). Nasal administration of pharmaceuticals has been shown to increase the amount of the compound available to the brain and reduce the levels in the systemic circulation while achieving higher concentrations of the drug in the body in less time. Furthermore, nasal administration achieves a desired effect at a lower concentration and subsequently reduces potential harmful side effects systemically associated with the inhalant compound (72, 73). For these beneficial reasons, in recent years a significant amount of common use drugs (i.e. Influenza vaccine and Insulin) have been in development for nasal administration. In this aim both Prog and ent-Prog are concentrated into a nasal delivery system that improves bioavailability in the brain and reduces levels in the systemic circulation. Nasal inhalants are a much more practical means of a field deliverable for military personnel and other high risk occupations or activities (i.e. sporting events).

Experimental Design

Drug Dose Response with Intranasal Administration

Subjects

To determine the optimal dose of Prog and ent-Prog when delivered IN in a model of mTBI 176 Sprague-Dawley rats at 280 grams are used.

Design

The dose response for IN administration is established using the same optimal drug formulation, animal groups and treatment time points outlined in Specific Aim 1. The difference in the drug concentrations administered IN compared to IP given that past data has shown that administration of a lower concentration of a given lipophilic drug given IN is a more efficient means of getting the drug into the brain than higher concentrations delivered IP, significantly lower IN concentrations are given IN in this study. The most efficacious IP dose for each drug established in Specific Aim 1 is used as the starting point for IN administration. From this starting concentration both Prog and ent-Prog are diluted to two lower concentrations based on the results of bioavailability studies outlined in Specific Aim 1. Statistical comparisons are made between IN and IP efficacy to determine if an IN deliverable is advantageous for treating mTBI.

Molecular Studies

Table 1 above shows a breakdown of the animals used in the Molecular Studies. Animal use and design is the same as in Example 7.

Serum Analysis

These studies are carried out with the same design as in Example 7.

Brain Tissue Analysis

These studies are carried out with the same design as in Example 7

Imaging Studies

These studies are carried out with the same design as Example 7.

Cognitive and Motor Behavioral Studies

These studies are carried out with the same design as in Example 7. Table 2 above shows a breakdown of the animals used in the Cognitive and Motor Behavioral Studies. Animal use and design is the same as in Example 7.

Example 9

Specific Aim

Determine the extent to which prophylactic and post-acute treatments with Progesterone and its Enantiomer reduce pathology associated with Repetitive Mild Traumatic Brain Injury.

Hypothesis

Prophylactic intranasal administration of the neurosteroids, Prog and ent-Prog prior to each of four repetitive mTBIs will prevent behavioral abnormalities and reduce pathological markers associated with poor long term outcomes.

Rationale

Experimental Design

Neurosteroid Administration for Repetitive mTBI

Neurosteroid Efficacy Studies

Repetitive mTBI has been associated with initial behavioral abnormalities including but not limited to; memory impairment, balance deficits and depression/anxiety disorders (50). Repetitive mTBI has been postulated to lead to early-onset dementia similar to that seen in AD patients with increased rates of suicide (54, 57). Like that seen in the temporal lobes of AD patients, individuals who have had repetitive mTBI have TDP-43-positive-tauopathy (64) and elevated levels of A$\beta$ amyloid (20, 62). The work in this aim is designed to treat each mTBI either prophylactically or in the post-acute phase to determine if Prog or ent-Prog can ameliorate the effects of repetitive TBI on behavior and molecular pathology.

Subjects

To determine if IN administration of Prog and ent-Prog are preventative and or protective in a model of repetitive mTBI 208 Sprague-Dawley rats weighing 280 grams are used.

Design

Animals are placed into 4 separate groups; treatment associated with first injury only, treatment associated with first and second injuries, treatment associated with first, second and third injuries, treatment associated with four injuries. As in Specific Aims 1 and 2 some groups will receive only prophylactic treatment (optimal IN administration time established Specific Aim 2) and others only post-acute treatment. The most efficacious IN dosage established for both prophylactic and post-acute treatment in Specific Aim 2 are administered to all animal groups.

Molecular Studies

Serum Analysis

These studies are carried out with the same design as Specific Aim 1 and include analysis after each successive injury.

Brain Tissue Analysis

Brain tissue from the penumbral region of the impact and the hippocampus is collected and processed as previously described in Specific Aim 1. Western analysis is performed using antibodies for hyper-phosphorylated tau (Thermo Scientific, Rockford, Ill.), TDP-43 (GenTex, Irvine, Calif.) and A$\beta$ amyloid (GeneScript, Piscataway, N.J.). All pathological markers are analyzed at 72 hours (n=4/group) and 14 days (n=4/group) following the 4 wk injury period.

Imaging Studies

These studies are carried out with the same design as Specific Aim 1 and include analysis after each successive injury.

Cognitive and Motor Behavioral Studies

The same behavioral studies outlined in the previous aims and discussed in Facilities and Equipment will be used in this specific aim. However, behavioral analysis will be ongoing for each group of animals throughout the 4 week study design no matter how many injuries the animal received including out to 72 hours following the designated time point of the 4$^{th}$ and final injury. An n=8 for each group is used for behavioral analysis. These same animals are used for the molecular analysis outlined above.

Side Effect Studies

Drugs are administered at multiple times. Given that the potential daily use of prophylactic ent-Prog for high risk occupations and that ent-Prog may be a safer deliverable than Prog due to identifiable side effects associated with the reproductive system and blood coagulation the work in this aim will determine if neurosteroids have side effects when administered multiple times and make a comparison between the Prog and ent-prog. The experiments in this aim are designed to compare issues of safety in animal groups that receive 1, 2, 3 or 4 drug treatments over a 4 wk time frame. Given that the same number of drug injections are administered as a prophylactic for post-acute treatment, only the potential harmful side effects are evaluated when treating in a prophylactic manner. The safety studies in this aim may be used to establish the effects of the drugs being administered on blood coagulation. Future work with more animals will have to be performed for safety characterization of the reproductive system where tissues can be collected at various time points.

Subjects

Serum coagulation assays: Blood is collected from half of the animals in this study at 6, 24 and 48 hrs after each injury for each treatment group and shams. Plasma is isolated and assayed for extrinsic and intrinsic clotting times. Plasma clotting times from all animal groups are compared to determine if neurosteroid treatments increase coagulation after multiple treatments. Briefly, A microplate-based blood coagulation assay described by Pratt and Monroe (85) is performed by adding 30 µl plasma and 30 µl buffer (20 mM HEPES, 150 mM NaCl, 0.1% polyethylene glycol (PEG), pH 7.4) to wells of microplate which are then incubated at 25° C. for 2 min. Clotting is initiated by adding 30 µl of 5% thromboplastin in 25 mM CaCl$_2$ for the Prothrombin Time Test (extrinsic clotting cascade) and 30 µl activated partial thromboplastin reagent for the Activated Partial Thromboplastin Time Test (intrinsic clotting cascade). The increase in the turbidity of plasma is measured by the change in absorbance at 405 nm.

Table 4 below shows a breakdown of the animals used in the Molecular, Cognitive and Motor Behavioral and Safety Studies in this aim. (Total=208 animals).

TABLE 4

Animal Use: Repetitive mTBI

| Group | Single Injury | Two Injuries | Three Injuries | Four Injuries |
|---|---|---|---|---|
| ent-Prog Prophylactic | n = 8 | n = 8 | n = 8 | n = 8 |
| ent-Prog Post-acute | n = 8 | n = 8 | n = 8 | n = 8 |
| Prog Prophylactic | n = 8 | n = 8 | n = 8 | n = 8 |
| Prog Post-acute | n = 8 | n = 8 | n = 8 | n = 8 |
| Vehicle Prophylactic | n = 8 | n = 8 | n = 8 | n = 8 |
| Vehicle Post-acute | n = 8 | n = 8 | n = 8 | n = 8 |
| Sham | n = 4 | n = 4 | n = 4 | n = 4 |

Statistical Techniques for Examples 1, 2, 3, 4, 5, 6, 7, 8 and 9

Alternative Techniques for Examples 1, 2, 3, 4, 5, 6, 7, 8 and 9

Drug Formulation

Many formulae are available for improving drug solubility for intranasal administration. Based on past use of cyclodextrin and carbopol for solubilizing Prog these two compounds should be useful for solubilizing ent-Prog. However, PEG has the potential to solubilize Prog and enhance brain uptake through intranasal delivery. PEG has no reported harmful side effects. Therefore, PEG may be used as a solvent.

Markers

The serum biomarkers and brain pathological markers were chosen for analysis based on past experimental findings primarily in the laboratories of the Principal and Co-Investigators as well as collaborators (Banyan Biomarkers, Inc.). However, there are many other serum and brain markers that may be regulated after mTBI (i.e. p53, NFκβ, S-Nitrosocysteine, MAP-2). With regards to brain pathological markers of Alzheimer's-like pathology in Specific Aim 3 it appears that these are the best options based on numerous previously reported findings in this field of research.

Analysis Technique

Our model of repetitive mild traumatic brain injury proposes to evaluate brain pathological markers in animals that get either 1, 2 or 3 mTBIs only at the same time points (72 hours and 14 d) after those animals that get a 4$^{th}$ and final mTBI. The problem with this design is that the time point of analysis following a given number of injuries is significantly different. An advantage of this design is that is that it makes it possible to determine if longer time periods after a given number of injuries shows an increased abundance in deleterious markers.

Example 10

Nasal Solution

An example of a nasal solution according to one embodiment of the present invention is described below. A 1% Tween 80 may be combined with solution of ent-Prog. That mixture is then combined with a quantity of isotonic saline sufficient to bring the total volume to 50 mL. The solution is sterilized by being passed through a 0.2 micron Millipore filter.

Example 11

Nasal Gel

An example of a nasal gel according to one embodiment of the present invention is described below. 250 mL of isotonic saline are heated to 80° C. and 1.5 g of Methocel are added, with stirring. The resultant mixture is allowed to stand at room temperature for 2 hours. Then, 100 mg of ent-progesterone are mixed together with 1 mg of Tween 80. The ent-progesterone/Tween mixture and a quantity of isotonic saline sufficient to bring the total volume to 500 ml are added to the gel and thoroughly mixed.

REFERENCES

The following references are referred to above and are incorporated herein by reference:
1. Pan, D. S., Liu, W. G., Yang, X. F., and Cao, F. (2007) Inhibitory effect of progesterone on inflammatory factors after experimental traumatic brain injury, *Biomed Environ Sci* 20, 432-438.
2. Jiang, C., Wang, J., Li, X., Liu, C., Chen, N., and Hao, Y. (2009) Progesterone exerts neuroprotective effects by inhibiting inflammatory response after stroke, *Inflamm Res* 58, 619-624.

3. Roof, R. L., Duvdevani, R., and Stein, D. G. (1992) Progesterone treatment attenuates brain edema following contusion injury in male and female rats, *Restor Neurol Neurosci* 4, 425-427.
4. Djebaili, M., Guo, Q., Pettus, E. H., Hoffman, S. W., and Stein, D. G. (2005) The neurosteroids progesterone and allopregnanolone reduce cell death, gliosis, and functional deficits after traumatic brain injury in rats, *J Neurotrauma* 22, 106-118.
5. Cutler, S. M., Cekic, M., Miller, D. M., Wali, B., VanLandingham, J. W., and Stein, D. G. (2007) Progesterone improves acute recovery after traumatic brain injury in the aged rat, *J Neurotrauma* 24, 1475-1486.
6. VanLandingham, J. W., Cekic, M., Cutler, S., Hoffman, S. W., and Stein, D. G. (2007) Neurosteroids reduce inflammation after TBI through CD55 induction, *Neurosci Lett* 425, 94-98.
7. Wright, D. W., Kellermann, A. L., Hertzberg, V. S., Clark, P. L., Frankel, M., Goldstein, F. C., Salomone, J. P., Dent, L. L., Harris, O. A., Ander, D. S., Lowery, D. W., Patel, M. M., Denson, D. D., Gordon, A. B., Wald, M. M., Gupta, S., Hoffman, S. W., and Stein, D. G. (2007) ProTECT: a randomized clinical trial of progesterone for acute traumatic brain injury, *Ann Emerg Med* 49, 391-402, 402 e391-392.
8. Xiao, G., Wei, J., Yan, W., Wang, W., and Lu, Z. (2008) Improved outcomes from the administration of progesterone for patients with acute severe traumatic brain injury: a randomized controlled trial, *Crit Care* 12, R61.
9. Stein, D. G. (2011) Is progesterone a worthy candidate as a novel therapy for traumatic brain injury?, *Dialogues Clin Neurosci* 13, 352-359.
10. Meaney, D. F., and Smith, D. H. (2011) Biomechanics of concussion, *Clin Sports Med* 30, 19-31, vii.
11. Chen, A. J., and D'Esposito, M. (2010) Traumatic brain injury: from bench to bedside [corrected] to society, *Neuron* 66, 11-14.
12. Tanielian, T. L., Jaycox, L., and Rand Corporation. (2008) *Invisible wounds of war: psychological and cognitive injuries, their consequences, and services to assist recovery*, RAND, Santa Monica, Calif.
13. Kennedy, J. E., Jaffee, M. S., Leskin, G. A., Stokes, J. W., Leal, F. O., and Fitzpatrick, P. J. (2007) Posttraumatic stress disorder and posttraumatic stress disorder-like symptoms and mild traumatic brain injury, *J Rehabil Res Dev* 44, 895-920.
14. Oquendo, M. A., Friend, J. M., Halberstam, B., Brodsky, B. S., Burke, A. K., Grunebaum, M. F., Malone, K. M., and Mann, J. J. (2003) Association of comorbid posttraumatic stress disorder and major depression with greater risk for suicidal behavior, *Am J Psychiatry* 160, 580-582.
15. Gibson, C. L., Constantin, D., Prior, M. J., Bath, P. M., and Murphy, S. P. (2005) Progesterone suppresses the inflammatory response and nitric oxide synthase-2 expression following cerebral ischemia, *Exp Neurol* 193, 522-530.
16. Gibson, C. L., and Murphy, S. P. (2004) Progesterone enhances functional recovery after middle cerebral artery occlusion in male mice, *J Cereb Blood Flow Metab* 24, 805-813.
17. Shahrokhi, N., Khaksari, M., Soltani, Z., Mahmoodi, M., and Nakhaee, N. (2010) Effect of sex steroid hormones on brain edema, intracranial pressure, and neurologic outcomes after traumatic brain injury, *Can J Physiol Pharmacol* 88, 414-421.
18. O'Connor, C. A., Cernak, I., Johnson, F., and Vink, R. (2007) Effects of progesterone on neurologic and morphologic outcome following diffuse traumatic brain injury in rats, *Exp Neurol* 205, 145-153.
19. Kiraly, M., and Kiraly, S. J. (2007) Traumatic brain injury and delayed sequelae: a review—traumatic brain injury and mild traumatic brain injury (concussion) are precursors to later-onset brain disorders, including early-onset dementia, *ScientificWorldJournal* 7, 1768-1776.
20. Tran, H. T., LaFerla, F. M., Holtzman, D. M., and Brody, D. L. (2011) Controlled cortical impact traumatic brain injury in 3× Tg-AD mice causes acute intra-axonal amyloid-beta accumulation and independently accelerates the development of tau abnormalities, *J Neurosci* 31, 9513-9525.
21. Shultz, S. R., Bao, F., Omana, V., Chiu, C., Brown, A., and Cain, D. P. (2012) Repeated mild lateral fluid percussion brain injury in the rat causes cumulative long-term behavioral impairments, neuroinflammation, and cortical loss in an animal model of repeated concussion, *J Neurotrauma* 29, 281-294.
22. Pettus, E. H., Wright, D. W., Stein, D. G., and Hoffman, S. W. (2005) Progesterone treatment inhibits the inflammatory agents that accompany traumatic brain injury, *Brain Res* 1049, 112-119.
23. Fleminger, S., Oliver, D. L., Lovestone, S., Rabe-Hesketh, S., and Giora, A. (2003) Head injury as a risk factor for Alzheimer's disease: the evidence 10 years on; a partial replication, *J Neurol Neurosurg Psychiatry* 74, 857-862.
24. Collins, M. W., Grindel, S. H., Lovell, M. R., Dede, D. E., Moser, D. J., Phalin, B. R., Nogle, S., Wasik, M., Cordry, D., Daugherty, K. M., Sears, S. F., Nicolette, G., Indelicato, P., and McKeag, D. B. (1999) Relationship between concussion and neuropsychological performance in college football players, *JAMA* 282, 964-970.
25. Iverson, G. L., Gaetz, M., Lovell, M. R., and Collins, M. W. (2004) Cumulative effects of concussion in amateur athletes, *Brain Inj* 18, 433-443.
26. Lewandowski, L., Rieger, B., Smyth, J., Perry, L., and Gathje, R. (2009) Measuring post-concussion symptoms in adolescents: feasibility of ecological momentary assessment, *Arch Clin Neuropsychol* 24, 791-796.
27. Binder, L. M. (1986) Persisting symptoms after mild head injury: a review of the postconcussive syndrome, *J Clin Exp Neuropsychol* 8, 323-346.
28. Wang, C., and Swerdloff, R. S. (2010) Hormonal approaches to male contraception, *Curr Opin Urol* 20, 520-524.
29. Mauvais-Jarvis, P., Kuttenn, F., and Baudot, N. (1974) Inhibition of testosterone conversion to dihydrotestosterone in men treated percutaneously by progesterone, *J Clin Endocrinol Metab* 38, 142-147.
30. VanLandingham, J. W., Cutler, S. M., Virmani, S., Hoffman, S. W., Covey, D. F., Krishnan, K., Hammes, S. R., Jamnongjit, M., and Stein, D. G. (2006) The enantiomer of progesterone acts as a molecular neuroprotectant after traumatic brain injury, *Neuropharmacology* 51, 1078-1085.
31. VanLandingham, J. W., Cekic, M., Hoffman, S. W., Cutler, S., Ory, D., Gale, S., Covey, D. F., and Stein, D. G. (2012) Progesterone activates the pregnane x receptor to reduce edema following traumatic brain injury.
32. Condon, J. C., Hardy, D. B., Kovaric, K., and Mendelson, C. R. (2006) Up-regulation of the progesterone receptor (PR)-C isoform in laboring myometrium by activation of nuclear factor-kappaB may contribute to the onset of labor through inhibition of PR function, *Mol Endocrinol* 20, 764-775.
33. Condon, J. C., Jeyasuria, P., Faust, J. M., Wilson, J. W., and Mendelson, C. R. (2003) A decline in the levels of progesterone receptor coactivators in the pregnant uterus at 45. Guskiewicz, K. M., McCrea, M., Marshall, S. W., Cantu, R. C., Randolph, C., Barr, W., Onate, J. A., and Kelly, J. P. (2003) Cumulative effects associated with recurrent concussion in collegiate football players: the NCAA Concussion Study, *JAMA* 290, 2549-2555.

46. Schneiderman, A. I., Braver, E. R., and Kang, H. K. (2008) Understanding sequelae of injury mechanisms and mild traumatic brain injury incurred during the conflicts in Iraq and Afghanistan: persistent postconcussive symptoms and posttraumatic stress disorder, *Am J Epidemiol* 167, 1446-1452.

E., Stern, R. A., Nowinski, C. J., Cantu, R. C., Kowall, N. W., Perl, D. P., Hedley-Whyte, E. T., Price, B., Sullivan, C., Morin, P., Lee, H. S., Kubilus, C. A., Daneshvar, D. H., Wulff, M., and Budson, A. E. (2010) TDP-43 proteinopathy and motor neuron disease in chronic traumatic encephalopathy, *J Neuropathol Exp Neurol* 69, 918-929.

65. Abuznait, A. H., Cain, C., Ingram, D., Burk, D., and Kaddoumi, A. (2011) Up-regulation of P-glycoprotein reduces intracellular accumulation of beta amyloid: investigation of P-glycoprotein as a novel therapeutic target for Alzheimer's disease, *J Pharm Pharmacol* 63, 1111-1118.

66. van Assema, D. M., Lubberink, M., Bauer, M., van der Flier, W. M., Schuit, R. C., Windhorst, A. D., Comans, E. F., Hoetjes, N. J., Tolboom, N., Langer, O., Muller, M., Scheltens, P., Lammertsma, A. A., and van Berckel, B. N. (2011) Blood-brain barrier P-glycoprotein function in Alzheimer's disease, *Brain*.

67. Vogelgesang, S., Cascorbi, I., Schroeder, E., Pahnke, J., Kroemer, H. K., Siegmund, W., Kunert-Keil, C., Walker, L. C., and Warzok, R. W. (2002) Deposition of Alzheimer's beta-amyloid is inversely correlated with P-glycoprotein expression in the brains of elderly non-demented humans, *Pharmacogenetics* 12, 535-541.

68. Bartels, A. L., Willemsen, A. T., Kortekaas, R., de Jong, B. M., de Vries, R., de Klerk, O., van Oostrom, J. C., Portman, A., and Leenders, K. L. (2008) Decreased blood-brain barrier P-glycoprotein function in the progression of Parkinson's disease, PSP and MSA, *J Neural Transm* 115, 1001-1009.

69. Kooij, G., Backer, R., Koning, J. J., Reijerkerk, A., van Horssen, J., van der Pol, S. M., Drexhage, J., Schinkel, A., Dijkstra, C. D., den Haan, J. M., Geijtenbeek, T. B., and de Vries, H. E. (2009) P-glycoprotein acts as an immunomodulator during neuroinflammation, *PLoS One* 4, e8212.

70. Kushwaha, S., RK, K., and AK, R. (2011) Advances in nasal trans-mucosal drug delivery, *Journal of Applied Pharmaceutical Science* 1, 21-28.

71. Ilium, L. (2000) Transport of drugs from the nasal cavity to the central nervous system, *Eur J Pharm Sci* 11, 1-18.

72. Hanson, L. R., Roeytenberg, A., Martinez, P. M., Coppes, V. G., Sweet, D. C., Rao, R. J., Marti, D. L., Hoekman, J. D., Matthews, R. B., Frey, W. H., 2nd, and Panter, S. S. (2009) Intranasal deferoxamine provides increased brain exposure and significant protection in rat ischemic stroke, *J Pharmacol Exp Ther* 330, 679-686.

73. Kime, P. (2011) Nasal spray may prevent onset of seasickness, *Navy Times*.

74. McKinlay, A., Bishop, A., and McLellan, T. (2011) Public knowledge of 'concussion' and the different terminology used to communicate about mild traumatic brain injury (MTBI), *Brain Inj* 25, 761-766.

75. Fehm, H. L., Perras, B., Smolnik, R., Kern, W., and Born, J. (2000) Manipulating neuropeptidergic pathways in humans: a novel approach to neuropharmacology?, *Eur J Pharmacol* 405, 43-54.

76. Rockhill, C. M., Fann, J. R., Fan, M. Y., Hollingworth, W., and Katon, W. J. (2010) Healthcare costs associated with mild traumatic brain injury and psychological distress in children and adolescents, *Brain Inj* 24, 1051-1060.

77. Hua, F., Wang, J., Ishrat, T., Wei, W., Atif, F., Sayeed, I., and Stein, D. G. (2011) Genomic profile of Toll-like receptor pathways in traumatically brain-injured mice: effect of exogenous progesterone, *J Neuroinflammation* 8, 42.

78. Mantzoros, C. S., Georgiadis, E. I., and Trichopoulos, D. (1995) Contribution of dihydrotestosterone to male sexual behaviour, *Bmj* 310, 1289-1291.

79. Carson, C., 3rd, and Rittmaster, R. (2003) The role of dihydrotestosterone in benign prostatic hyperplasia, *Urology* 61, 2-7.

80. Cai, L. Q., Fratianni, C. M., Gautier, T., and Imperato-McGinley, J. (1994) Dihydrotestosterone regulation of semen in male pseudohermaphrodites with 5 alpha-reductase-2 deficiency, *The Journal of clinical endocrinology and metabolism* 79, 409-414.

81. Kelleher, C. C. (1990) Clinical aspects of the relationship between oral contraceptives and abnormalities of the hemostatic system: relation to the development of cardiovascular disease, *American journal of obstetrics and gynecology* 163, 392-395.

82. Vandenbroucke, J. P., Rosing, J., Bloemenkamp, K. W., Middeldorp, S., Helmerhorst, F. M., Bouma, B. N., and Rosendaal, F. R. (2001) Oral contraceptives and the risk of venous thrombosis, *The New England journal of medicine* 344, 1527-1

89. Tas, E., Ozkan, Y., Savaser, A., and Baykara, T. (2004) In vitro and ex vivo permeation studies of chlorpheniramine maleate gels prepared by carbomer derivatives, *Drug Dev Ind Pharm* 30, 637-647.

90. Czeiter, E., Mondello, S., Kovacs, N., Sandor, J., Gabrielli, A., Schmid, K., Tortella, F., Wang, K. K., Hayes, R. L., Barzo, P., Ezer, E., Doczi, T., and Buki, A. (2012) Brain injury biomarkers may improve the predictive power of the IMPACT outcome calculator, *J Neurotrauma* 29, 1770-1778.

91. Cox, C. D., West, E. J., Liu, M. C., Wang, K. K., Hayes, R. L., and Lyeth, B. G. (2008) Dicyclomine, an M1 muscarinic antagonist, reduces biomarker levels, but not neuronal degeneration, in fluid percussion brain injury, *J Neurotrauma* 25, 1355-1365.

92. de Souza Silva, M. A., Topic, B., Huston, J. P., and Mattern, C. (2008) Intranasal dopamine application increases dopaminergic activity in the neostriatum and nucleus accumbens and enhances motor activity in the open field, *Synapse* 62, 176-184.

93. van den Berg, M. P., Verhoef, J. C., Romeijn, S. G., and Merkus, F. W. (2004) Uptake of estradiol or progesterone into the CSF following intranasal and intravenous delivery in rats, *Eur J Pharm Biopharm* 58, 131-135.

While the present invention has been disclosed with references to certain embodiments, numerous modification, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method for treating one or more traumatic brain injuries in an individual comprising the following step:
   (a) administering a composition to an individual in need thereof by nasal administration,
   wherein the composition comprises ent-progesterone and one or more cyclodextrins, and
   wherein the molar ratio of ent-progesterone to the total amount of cyclodextrins in the composition is about 1:1.

2. The method of claim 1, wherein the composition is an aqueous solution.

3. The method of claim 1, wherein the composition is a gel.

4. The method of claim 1, wherein step (a) comprises spraying the composition into one or both nasal passages of the individual.

5. The method of claim 1, wherein step (a) comprises applying the composition to one or more surfaces of one or both nasal passages of the individual.

6. A method for treating one or more traumatic brain injuries in an individual comprising the following step:
   (a) administering a composition to an individual in need thereof by nasal administration,
   wherein the composition comprises ent-progesterone and a bioadhesive polymer, and
   wherein molar ratio of ent-progesterone to the bioadhesive polymer in the composition is about 1:1.

7. The method of claim 6, wherein the composition comprises one or more cyclodextrins.

8. The method of claim 6, wherein the composition is an aqueous solution.

9. The method of claim 6, wherein the composition is a gel.

10. The method of claim 6, wherein step (a) comprises spraying the composition into one or both nasal passages of the individual.

11. The method of claim 6, wherein step (a) comprises applying the composition to one or more surfaces of one or both nasal passages of the individual.

12. A composition comprising ent-progesterone and one or more cyclodextrins, wherein molar ratio of ent-progesterone to the total amount of cyclodextrins in the composition is about 1:1.

13. The composition of claim 12, wherein the composition is an aqueous solution.

14. The composition of claim 12, wherein the composition is a gel.

15. A composition comprising ent-progesterone and a bioadhesive polymer, wherein molar ratio of ent-progesterone to the bioadhesive polymer in the composition is about 1:1.

16. The composition of claim 15, wherein the composition is an aqueous solution.

17. The composition of claim 15, wherein the composition is a gel.

* * * * *